(12) United States Patent
Moss et al.

(10) Patent No.: US 11,730,563 B2
(45) Date of Patent: Aug. 22, 2023

(54) KNUCKLE JOINT ASSEMBLY FOR MEDICAL DEVICE SUPPORT SYSTEM

(71) Applicant: American Sterilizer Company, Mentor, OH (US)

(72) Inventors: Bernard John Moss, Perry, OH (US); Lance Clark Bellows, Painesville, OH (US)

(73) Assignee: American Sterilizer Company, Mentor, OH (US)

( * ) Notice: Subject to any disclaimer, the term of this patent is extended or adjusted under 35 U.S.C. 154(b) by 0 days.

(21) Appl. No.: 18/063,749

(22) Filed: Dec. 9, 2022

(65) Prior Publication Data

US 2023/0105016 A1  Apr. 6, 2023

Related U.S. Application Data

(62) Division of application No. 16/702,860, filed on Dec. 4, 2019, now Pat. No. 11,547,522.

(Continued)

(51) Int. Cl.
*A61B 90/50* (2016.01)
*F16M 13/02* (2006.01)
(Continued)

(52) U.S. Cl.
CPC .............. *A61B 90/50* (2016.02); *A61B 90/35* (2016.02); *F16M 13/022* (2013.01); *A61B 34/71* (2016.02);
(Continued)

(58) Field of Classification Search
CPC . A61B 90/50; A61B 90/35; A61B 2090/5025; A61B 2090/506; A61B 34/71;
(Continued)

(56) References Cited

U.S. PATENT DOCUMENTS 4,200,407 A * 4/1980 Bianco .................... B21B 31/07
                                                                    403/373
10,835,346 B2 * 11/2020 Bellows ................. A61B 50/28
(Continued)

FOREIGN PATENT DOCUMENTS

DE   102016005785 A1   11/2017
EP       3009728 A1    4/2016
(Continued)

OTHER PUBLICATIONS

International Search Report and Written Opinion for corresponding International Application PCT/US2019/064379 dated Mar. 26, 2020.
(Continued)

*Primary Examiner* — Todd M Epps
(74) *Attorney, Agent, or Firm* — Renner, Otto, Boisselle & Sklar, LLP

(57) ABSTRACT

Knuckle joint assembly for a medical device support system. The knuckle joint assembly includes a cartridge assembly that includes a cartridge housing and a rotary bearing. The cartridge housing includes a bore having a central axis and a bearing mount in the bore. The rotary bearing is press fitted in the bearing mount and configured to receive axially therethrough a spindle to rotatably support the spindle about the central axis. The knuckle joint assembly includes a retaining clip and a retaining pin. The retaining clip is selectively movable to disengage and engage a groove in a spindle to respectively support or release the spindle along a central axis. The retaining pin is movable between a first position to allow movement of the retaining clip between positions but prevent removal of the retaining clip, and a second position to block movement of the retaining clip from the engaged position.

18 Claims, 15 Drawing Sheets

Related U.S. Application Data

(60) Provisional application No. 62/799,202, filed on Jan. 31, 2019, provisional application No. 62/799,113, filed on Jan. 31, 2019, provisional application No. 62/799,096, filed on Jan. 31, 2019, provisional application No. 62/799,100, filed on Jan. 31, 2019.

(51) Int. Cl.
  *A61B 90/35* (2016.01)
  *A61B 34/00* (2016.01)
  *F16D 65/06* (2006.01)

(52) U.S. Cl.
  CPC ... *A61B 2034/715* (2016.02); *A61B 2090/506* (2016.02); *A61B 2090/508* (2016.02); *A61B 2090/5025* (2016.02); *F16D 65/065* (2013.01); *F16M 2200/022* (2013.01); *F16M 2200/041* (2013.01); *F16M 2200/066* (2013.01)

(58) Field of Classification Search
  CPC ........ A61B 2034/715; A61B 2090/508; F16M 13/022; F16M 2200/041; F16M 2200/066; F16M 2200/022
  USPC ..... 248/637, 642, 646, 674, 276.1; 403/161, 403/164, 52, 345
  See application file for complete search history.

(56) References Cited

U.S. PATENT DOCUMENTS

| | | | | |
|---|---|---|---|---|
| 10,874,476 | B2 * | 12/2020 | Bellows | A61B 50/28 |
| 10,966,796 | B2 * | 4/2021 | Bellows | A61B 90/30 |
| 10,993,778 | B2 * | 5/2021 | Bellows | F16M 13/027 |
| 11,173,009 | B2 * | 11/2021 | Bellows | A61B 90/35 |
| 11,547,522 | B2 * | 1/2023 | Moss | F16M 13/022 |
| 2017/0290725 | A1 | 10/2017 | Oginski et al. | |
| 2017/0304022 | A1 | 10/2017 | Oginski et al. | |
| 2017/0326738 | A1 | 11/2017 | Christiansen | |

FOREIGN PATENT DOCUMENTS

| | | |
|---|---|---|
| FR | 1441338 A | 6/1966 |
| WO | 200145627 A1 | 6/2001 |
| WO | 2003040609 A1 | 5/2003 |
| WO | 2016058707 A2 | 4/2016 |

OTHER PUBLICATIONS

Written Opinion of the International Preliminary Examining Authority (Second Written Opinion) for corresponding International Application PCT/US2019/064379 dated Feb. 16, 2021.

International Preliminary Report on Patentability for corresponding International Application PCT/US2019/064379 dated Apr. 30, 2021.

* cited by examiner

KNUCKLE JOINT ASSEMBLY FOR MEDICAL DEVICE SUPPORT SYSTEM

This application is a divisional of U.S. application Ser. No. 16/702,860 filed on Dec. 4, 2019, which claims priority to U.S. Patent Application No. 62/799,096 filed Jan. 31, 2019, U.S. Patent Application No. 62/799,100 filed Jan. 31, 2019, U.S. Patent Application No. 62/799,113 filed Jan. 31, 2019, and U.S. Patent Application No. 62/799,202 filed Jan. 31, 2019. These prior applications are incorporated herein by reference.

FIELD OF INVENTION

This application relates generally to a knuckle joint assembly for a medical device support system or carry system for use in, for example, a hospital examination room, a clinic, a surgery room or an emergency room, and more particularly to a knuckle joint assembly having a serviceable cartridge assembly and multiple safety mechanisms.

BACKGROUND

Medical device support systems or carry systems are used in health treatment settings such as hospital examination rooms, clinics, surgery rooms and emergency rooms. These systems may suspend or support any variety of medical devices or components including surgical lights, supply consoles, patient monitors, camera detector heads, medical instruments, ventilator systems, suction devices, among others. The support systems typically include a central shaft or support column that is suspended from the ceiling or mounted to a wall, one or more generally horizontal extension arms mounted for rotational movement about the shaft, and one or more load balancing arms, also known as spring arms or counterbalancing arms, that enable positioning of a medical device to a proper orientation relative to for example a patient operating table and healthcare professionals in the operating room.

The load balancing arm typically is rotatably connected to a knuckle joint assembly at the distal end of the extension arm. A housing of the knuckle joint assembly may include a bearing that receives a spindle of the load balancing arm thereby enabling rotatable movement of the load balancing arm relative to the knuckle joint housing of the extension arm. A retaining clip or key may be inserted into a slot in the knuckle joint housing to engage a circumferential groove in the spindle to maintain an axial position of the spindle. A retaining pin, plate or sleeve may be used to prevent backing out of the retaining clip from the slot. The knuckle joint assembly may also include a brake assembly to frictionally engage the spindle of the load balancing arm, and a slip ring to transmit power or data signals from cabling in the extension arm to the proximal end of the load balancing arm.

For knuckle joint assemblies in some medical device support systems or carry systems, there remain various shortcomings, drawbacks, and disadvantages relative to certain applications. Servicing the internal components of some knuckle joint assemblies presents several problems or potential problems. For example, the bearings of known knuckle joint assemblies are not easily replaceable or serviceable in the field. The reason for this is that the tolerances are built into the knuckle joint housing of the extension arm; thus, to service the bearings, typically the entire extension arm including its knuckle joint assembly must be removed and returned to the manufacturer or supplier. The bearings can then be removed and replaced with appropriate fitting and aligning equipment. This can create downtime for health treatment facilities especially those equipped with only a single medical device support system or a single extension arm or spring arm. Also, in some knuckle joint assemblies to remove the spring arm spindle, the retaining pin must first be moved out of the way of the retaining clip to allow the retaining clip to be removed from the slot to release the spring arm spindle. One problem or potential problem is that the retaining clip can be entirely withdrawn, i.e. separated, from the knuckle joint assembly, risking misplacement of the retaining clip or improper reinsertion of the retaining clip, for example, upside down instead of right side up.

Accordingly, there remains a need for further contributions in this area of technology.

SUMMARY OF INVENTION

The application relates to a knuckle joint assembly for a medical device support system, in which the knuckle joint assembly has a serviceable cartridge assembly and multiple safety mechanisms. The cartridge assembly includes a housing with a bearing fitted therein to rotatably support a spindle and is removably insertable into a knuckle joint housing for simplified servicing or replacement without for example having to disassemble and return an entire extension arm or medical device support system to the manufacturer or supplier. One safety mechanism includes a non-removable retaining clip in which a retaining pin either locks the retaining clip in a spindle groove to maintain an axial position of the spindle or allows movement of the retaining clip enough to release the spindle but prevents removal of the retaining clip from the knuckle joint assembly.

According to one aspect of the invention, a cartridge assembly for a knuckle joint housing of a medical device support system, includes a cartridge housing including a bore having a central axis and a bearing mount in the bore; and, a rotary bearing press fitted in the bearing mount and configured to receive axially therethrough a spindle to rotatably support the spindle about the central axis.

Embodiments of the invention may include one or more of the following additional features separately or in combination.

The cartridge housing may include a base with a threaded opening for receiving a threaded fastener to mount the cartridge housing to the knuckle joint housing.

The rotary bearing may be a needle roller bearing.

The cartridge assembly may further include a brake assembly cradled in a recess of the cartridge housing and including at least one brake pad selectively movable radially inward and radially outward relative to the central axis.

The brake assembly may include a C clamp brake assembly.

The recess may be defined by a flange projecting radially inwardly from a second bore of the cartridge housing, and the clamp brake assembly may be axially supported by the flange.

The least one brake pad may be selectively movable radially inward and radially outward to respectively increase and decrease a frictional braking force to a spindle rotatably supported in the rotary bearing.

The at least one brake pad may include first and second arc shape brake pads.

The first and second arc shape brake pads may be selectively movable toward and away from each other to respectively increase and decrease a frictional braking force to a spindle rotatably supported in the rotary bearing.

The cartridge assembly may further include an actuator configured to selectively move the at least one brake pad radially inward and radially outward relative to the central axis, the actuator being accessible from an opening in an outer surface of the cartridge housing.

The cartridge assembly may further include a retaining clip selectively movable between a disengaged position in which the retaining clip is disengaged from a groove in a spindle to allow movement of the spindle along the central axis, and an engaged position in which the retaining clip slidably engages the groove in the spindle to support the spindle in an axial position along the central axis.

The retaining clip may be supported by an upper surface of the cartridge housing.

The retaining clip may be movable in a first direction radially toward the central axis to slidably engage a groove in a spindle, and in a second direction radially away from the central axis to disengage the groove in the spindle.

The retaining clip may be supported by a radially protruding slot in an upper portion of the cartridge housing.

The radially protruding slot may include an axially supporting lower surface and laterally opposite upper guide surfaces that form respective laterally opposite gaps, wherein the heights of the gaps are greater than the height of the retaining clip to provide a slidable fit for the retaining clip.

The radially protruding slot may include laterally opposite side guide surfaces that form a gap, the width of which is slightly greater than the width of the retaining clip to provide a slidable fit for the retaining clip.

The cartridge assembly may further include a retaining pin movable between a first position in which the retaining pin allows movement of the retaining clip between the disengaged position and the engaged position but prevents removal of the retaining clip from the cartridge assembly, and a second position in which the retaining pin blocks movement of the retaining clip from the engaged position.

The retaining pin may have a pin axis and a minor OD and a major OD at different positions along the pin axis that correspond respectively to the first position and second position.

The retaining pin may be mounted within a hole in the cartridge housing for reciprocable movement between the first position and the second position.

The hole may have a central axis that is parallel to the central axis of the bore of the cartridge housing.

The retaining pin may be spring biased toward the second position.

The retaining pin may be bound for reciprocable movement beyond the second position by a ledge inside the hole.

The retaining pin may be bound for reciprocable movement beyond the first position by a set screw inside the hole.

The retaining clip may have a slot into which the retaining pin projects, the slot having a relatively narrower width and a relatively larger width, and the retaining clip may be selectively movable based on the width of the slot and whether the retaining pin is in the first position or the second position.

The slot may have a keyhole shape wherein a narrower portion of the keyhole corresponds to the narrower width of the slot and a round portion of the keyhole corresponds to the larger width of the slot.

The retaining pin in the first position may have a width that is less than the narrower width slot so that the retaining pin slides within the slot as the retaining clip is moved between the disengaged position and the engaged position.

The retaining pin in the second position may have a width that is greater than the narrower width slot so that the retaining pin is unable to slide from the larger width slot to the narrower width slot which blocks movement of the retaining clip from the engaged position.

The cartridge assembly may further include a retaining clip guide configured to restrain the retaining clip in two axes of motion including vertical motion and side to side motion so that the retaining clip moves along the direction of the slot.

The cartridge assembly may further include a female slip ring holder fastened to an upper surface of the cartridge housing and configured to hold a female slip ring in concentric relation to the central axis.

The cartridge assembly may further include a cable holder fastened to an upper surface of the cartridge housing and including a pass through hole configured to route a cable run along the central axis.

According to another aspect of the invention, a knuckle joint assembly for a medical device support system includes a knuckle joint housing including a cartridge assembly receptacle; and, a cartridge assembly removably insertable in the cartridge assembly receptacle, the cartridge assembly including a cartridge housing including a bore having a central axis and a bearing mount in the bore, and a rotary bearing press fitted in the bearing mount and configured to receive axially therethrough a spindle to rotatably support the spindle about the central axis.

Embodiments of the invention may include one or more of the following additional features separately or in combination.

The cartridge assembly receptacle may define an opening that has a vertical axis, and the cartridge assembly may be removably insertable into the opening so that the central axis of the cartridge assembly coincides with the vertical axis.

The opening may open vertically upward, and the cartridge assembly may be removably insertable vertically into the opening along the vertical axis.

The cartridge assembly receptacle may define an opening into which the cartridge assembly is removably insertable, and the cartridge assembly receptacle may include a flange at the bottom of the opening that supports the cartridge assembly in an axial position.

The cartridge housing may be configured to be fastened to the flange.

The flange may include a plurality of fastener through holes and the cartridge housing may include at least two threaded openings that axially align with two of the plurality of fastener through holes when inserted in the cartridge assembly receptacle, and the cartridge housing may be fastened to the flange via respective fasteners passing through the respective through holes and engaging the threaded openings.

According to another aspect of the invention, a knuckle joint assembly for a medical device support system includes a knuckle joint housing including a rotary bearing having a central axis and configured to receive axially therethrough a spindle to rotatably support the spindle about the central axis; a retaining clip selectively movable between a disengaged position in which the retaining clip is disengaged from a groove in a spindle to allow movement of the spindle along the central axis, and an engaged position in which the retaining clip slidably engages the groove in the spindle to support the spindle in an axial position along the central axis; and, a retaining pin movable between a first position in which the retaining pin allows movement of the retaining clip between the disengaged position and the engaged position but prevents removal of the retaining clip from the knuckle joint assembly, and a second position in which the retaining pin blocks movement of the retaining clip from the engaged position.

Embodiments of the invention may include one or more of the following additional features separately or in combination.

The retaining clip may be supported by an upper surface of the knuckle joint housing.

The retaining clip may be movable in a first direction radially toward the central axis to slidably engage a groove in a spindle, and in a second direction radially away from the central axis to disengage the groove in the spindle.

The retaining clip may be supported by a radially protruding slot in an upper portion of the knuckle joint housing.

The radially protruding slot may include an axially supporting lower surface and laterally opposite upper guide surfaces that form respective laterally opposite gaps, wherein the heights of the gaps are greater than the height of the retaining clip to provide a slidable fit for the retaining clip.

The radially protruding slot may include laterally opposite side guide surfaces that form a gap, the width of which is slightly greater than the width of the retaining clip to provide a slidable fit for the retaining clip.

The retaining pin may have a pin axis and a minor OD and a major OD at different positions along the pin axis that correspond respectively to the first position and second position.

The retaining pin may be mounted within a hole in the knuckle joint housing for reciprocable movement between the first position and the second position.

The hole may have a central axis that is parallel to the central axis of the rotary bearing.

The retaining pin may be spring biased toward the second position.

The retaining pin may be bound for reciprocable movement beyond the second position by a ledge inside the hole.

The retaining pin may be bound for reciprocable movement beyond the first position by a set screw inside the hole.

The retaining clip may have a slot into which the retaining pin projects, the slot having a relatively narrower width and a relatively larger width, and the retaining clip may be selectively movable based on the width of the slot and whether the retaining pin is in the first position or the second position.

The slot may have a keyhole shape wherein a narrower portion of the keyhole corresponds to the narrower width of the slot and a round portion of the keyhole corresponds to the larger width of the slot.

The retaining pin in the first position may have a width that is less than the narrower width slot so that the retaining pin slides within the slot as the retaining clip is moved between the disengaged position and the engaged position.

The retaining pin in the second position may have a width that is greater than the narrower width slot so that the retaining pin is unable to slide from the larger width slot to the narrower width slot which blocks movement of the retaining clip from the engaged position.

The knuckle joint assembly may further include a retaining clip guide configured to restrain the retaining clip in two axes of motion including vertical motion and side to side motion so that the retaining clip moves along the direction of the slot.

The knuckle joint assembly may further comprise a knuckle joint housing cover connectable to the knuckle joint housing to cover the knuckle joint housing, wherein when the retaining clip is in a disengaged position the retaining clip blocks the cover from being connectable to the knuckle joint housing.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention.

DETAILED DESCRIPTION

Figure 1:
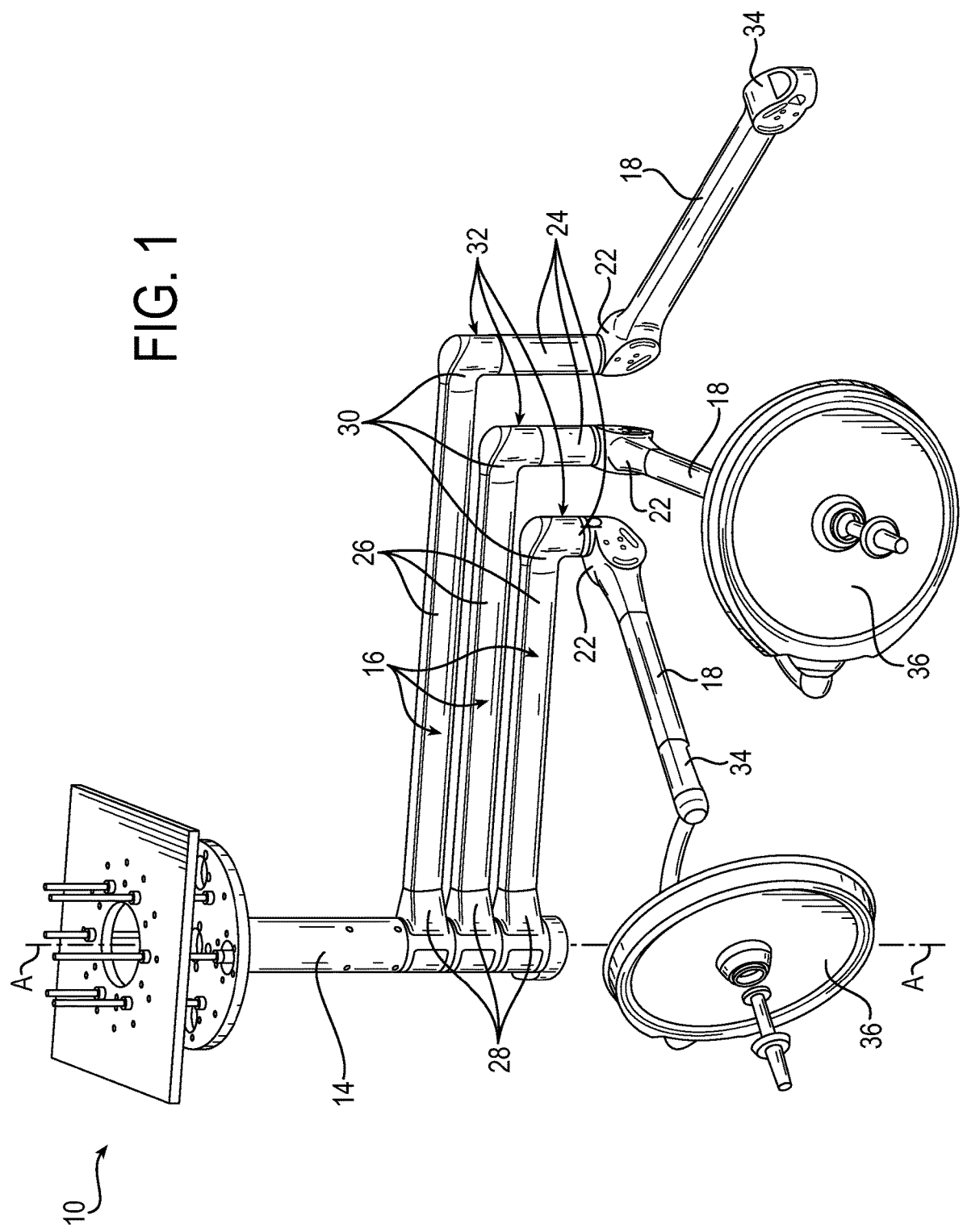
FIG. 1 is a perspective view of a medical device support system in accordance with an embodiment of the invention.

While the present invention can take many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications of the described embodiments, and any further applications of the principles of the invention as described herein, are contemplated as would normally occur to one skilled in the art to which the invention relates.

FIG. 1 shows a medical device support system 10 in accordance with an embodiment of the invention. The medical device support system 10 includes a central shaft or support column 14 that is suspended from the ceiling, and three generally horizontal extension arms 16 mounted to the shaft 14 for rotational movement about the shaft 14 via proximal hubs 28 of the extension arms 16. The central shaft 14 could be mounted to a wall or stand rather than the ceiling. Three load balancing arms 18, which are also referred to as counterbalancing arms, are mounted to the respective extension arms 16. In the FIG. 1 embodiment, the extension arms 16 each include at their distal end 30 a knuckle joint assembly 32 that rotatably supports a spindle 24 of a respective load balancing arm 18 at a proximal end 22 of the load balancing arm 18. The distal end of each load balancing arm 18 is configured with a suitable support hub 34 to support a medical device load 36. The medical device load 36 may include a surgical light as shown, or a supply console, a patient monitor, a camera detector head, a medical instrument, a ventilator system, a suction device, among others. A control console, if provided, may provide controls for navigation of a medical instrument that is either coupled to or remote from the load balancing arm 18. The knuckle joint assembly 32 may be provided with a rotational stop 58 to limit rotation of a spindle stop 60, and thus limiting rotation of the load balancing arm 18.

Figure 2:
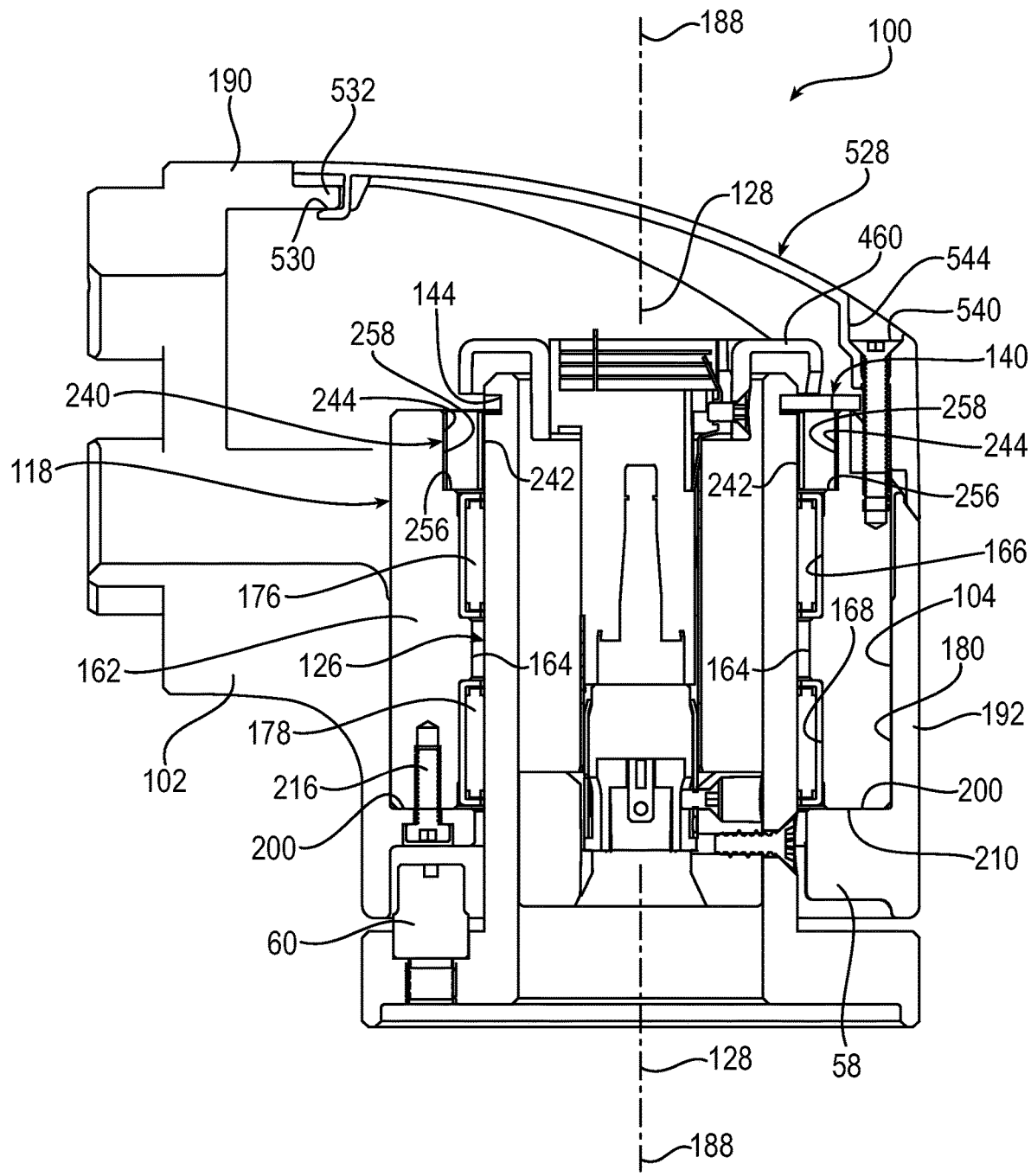
FIG. 2 is a side cross section view of a knuckle joint assembly in accordance with an embodiment of the invention.
Figure 3:
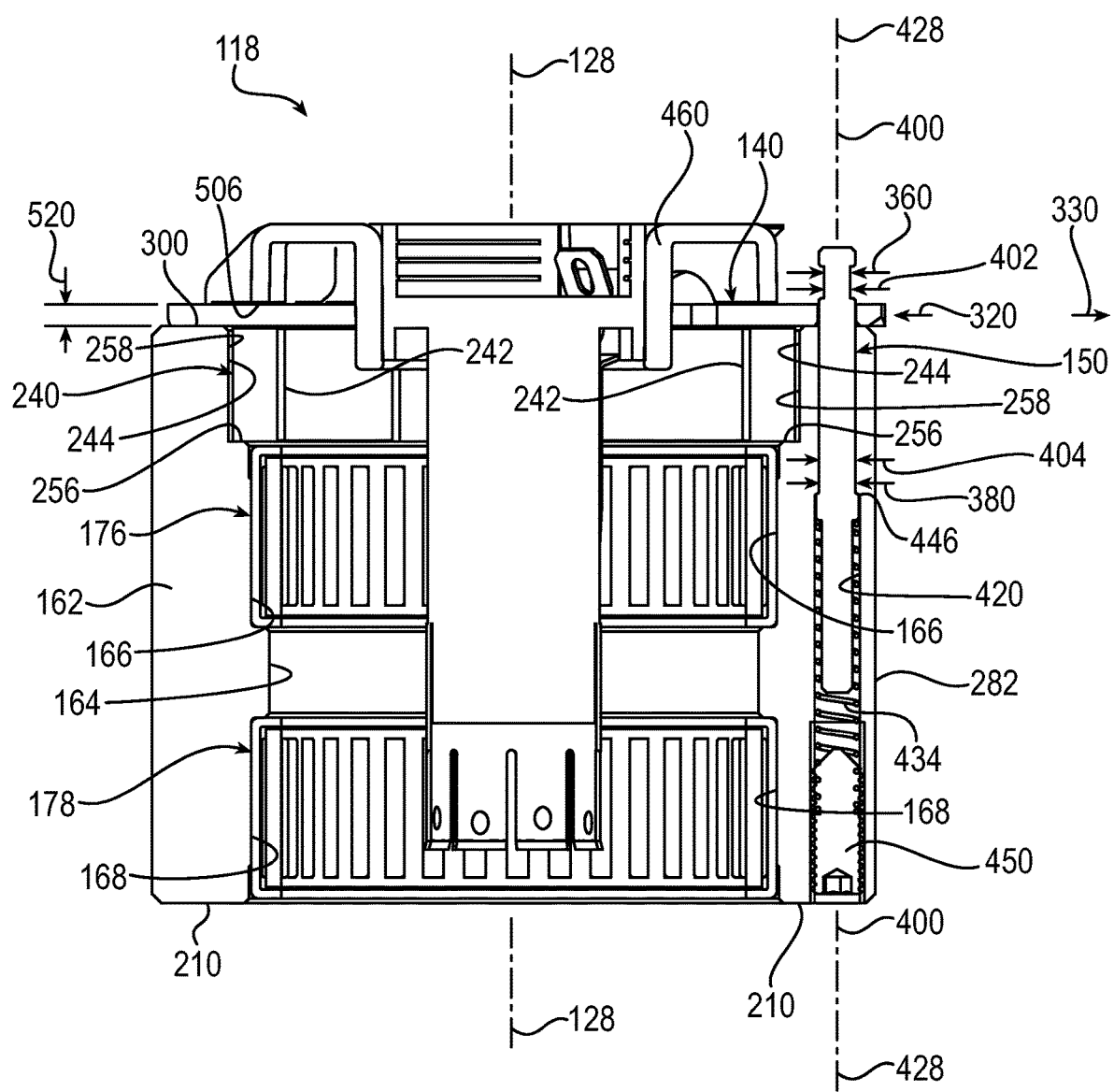
FIG. 3 is a side cross section view of a cartridge assembly in accordance with an embodiment of the invention.
Figure 4:
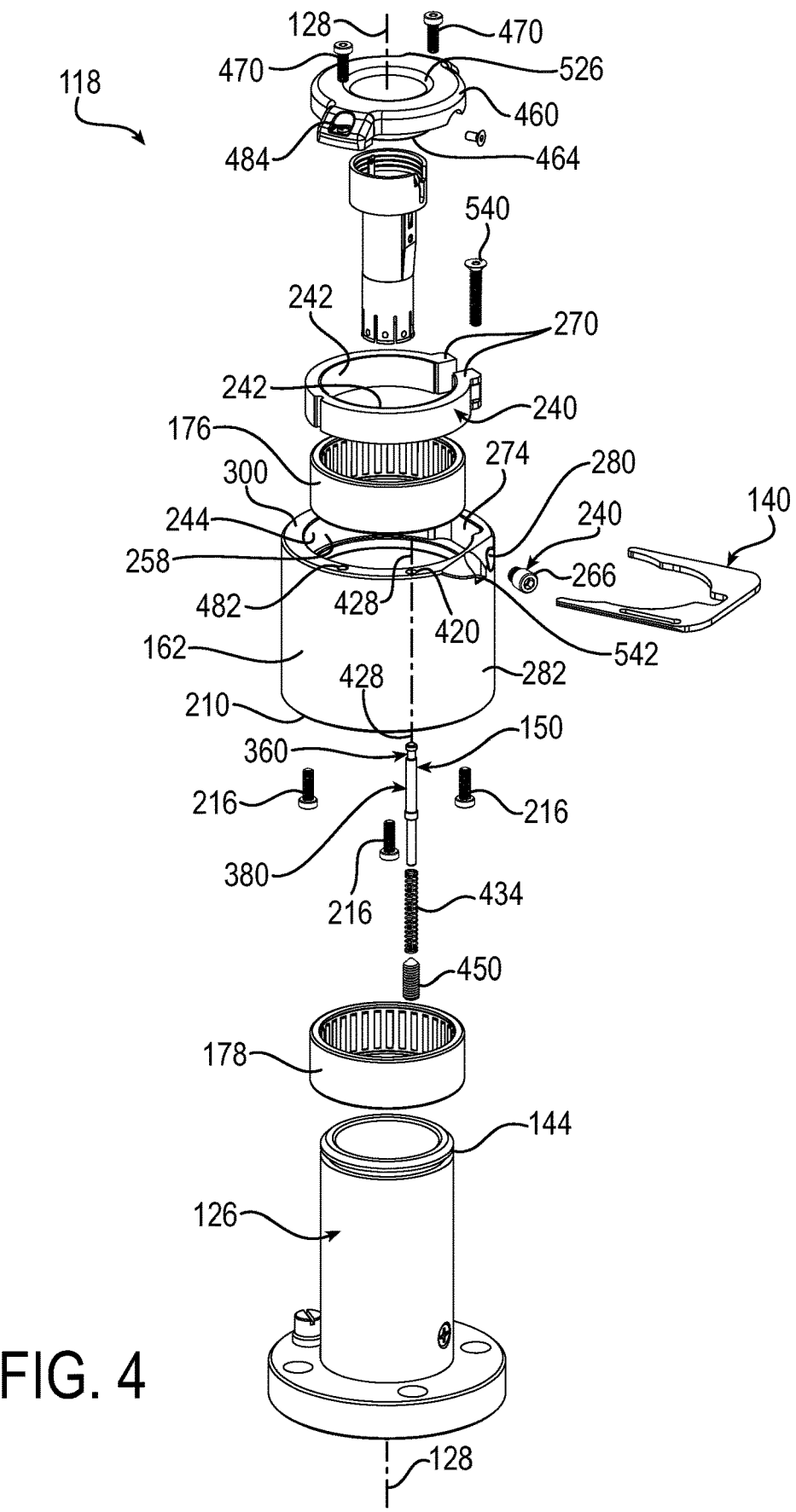
FIG. 4 is an exploded view of the FIG. 3 cartridge assembly and a spindle rotatably supportable by the cartridge assembly.

Turning now to FIGS. 2-4, there is shown a knuckle joint assembly 100, such as the knuckle joint assembly 32 of the medical device support system 10, in accordance with an embodiment of the invention. The knuckle joint assembly 100 includes a knuckle joint housing 102 including a cartridge assembly receptacle 104, and a cartridge assembly 118 removably insertable in the cartridge assembly receptacle 104. The cartridge assembly 118 rotatably supports a spindle 126, for example the spindle 24 of a respective load balancing arm 18 in FIG. 1, about a central axis 128. A retaining clip 140 is movable between an engaged position to slidably engage a groove 144 in the spindle 126 to support the spindle 126 in an axial position along the central axis 128, and a disengaged position in which the retaining clip 140 is disengaged from the groove 144 to allow movement of the spindle 126 along the central axis 128. A retaining pin 150 is movable between a first or lower position in which the retaining pin 150 allows movement of the retaining clip 140 between a disengaged position and its engaged position but prevents removal of the retaining clip 140 from the knuckle joint assembly 100, and a second or upper position in which the retaining pin 150 blocks movement of the retaining clip 140 from the engaged position. As will be described in greater detail below, the cartridge assembly 118 simplifies servicing or replacement without having to disassemble and return an entire extension arm 16 or medical device support system 10 to a manufacturer or supplier, and the retaining pin 150 prevents misplacement of the retaining clip 140 or improper reinsertion of the retaining clip 140.

Figure 8:
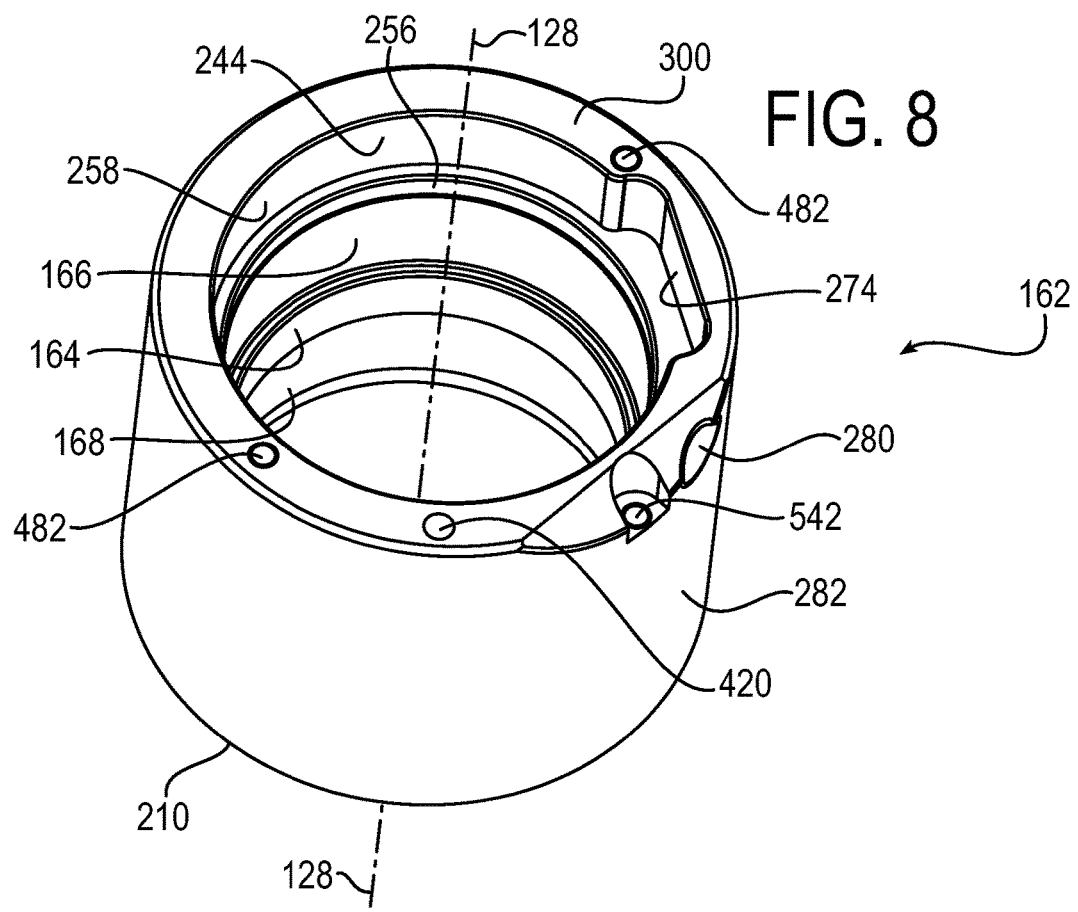
FIG. 8 is a top perspective view of a cartridge housing of the FIG. 3 cartridge assembly.
Figure 9:
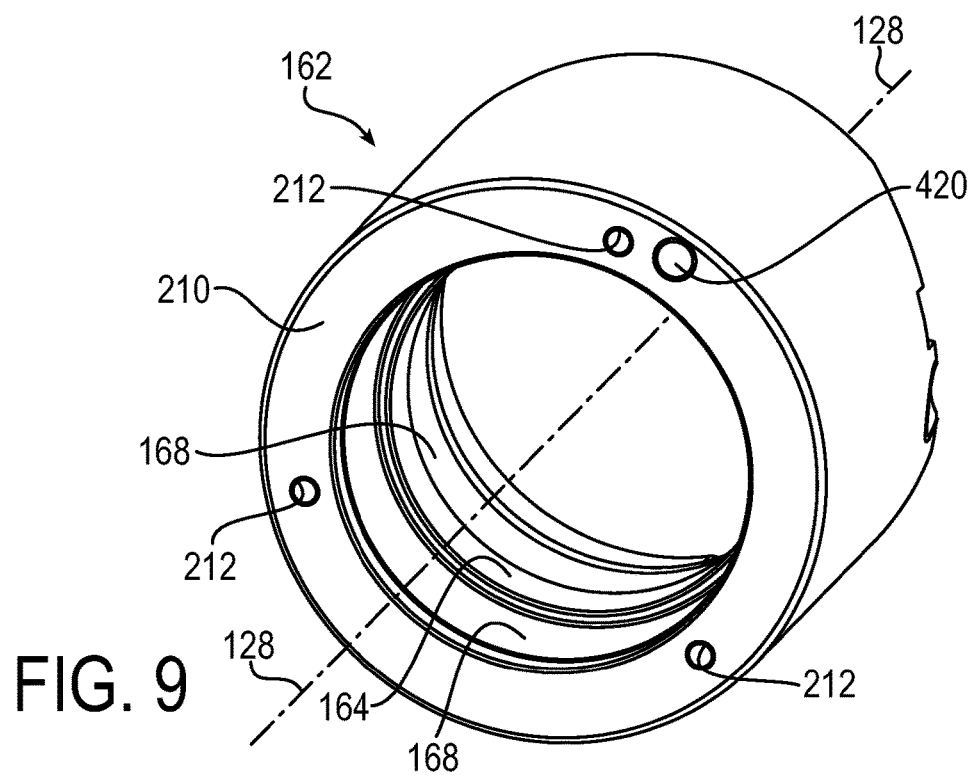
FIG. 9 is a bottom perspective view of a cartridge housing of the FIG. 3 cartridge assembly.

As shown in FIGS. 2 and 8-9, the cartridge assembly 118 includes a cartridge housing 162 having a generally annular shape in top plan view and defining a bore 164 having the central axis 128 as its center. Upper and lower bearing mounts 166, 168 are provided in the bore 164. Upper and lower rotary bearings 176, 178 are press fitted in the respective bearing mounts 166, 168. The rotary bearings 176, 178 receive axially therethrough the spindle 126 to rotatably support the spindle 126 about the central axis 128. The bearing mounts 166, 168 can be in the form of annular recesses as shown in FIGS. 8 and 9, or any other suitable structure for securing a bearing. Any type of rotary bearing 176, 178 may be used to facilitate the relative rotational movement between the cartridge housing 162 and the spindle 126, including for example needle roller bearings as shown, or ball bearings, sleeve bearings, bushings, rotary joints and/or swivel joints. Although two bearing mounts 166, 168 and two rotary bearings 176, 178 are illustrated, those skilled in the art will appreciate that a single bearing mount and a single bearing may also be suitable in certain applications.

Figure 7:
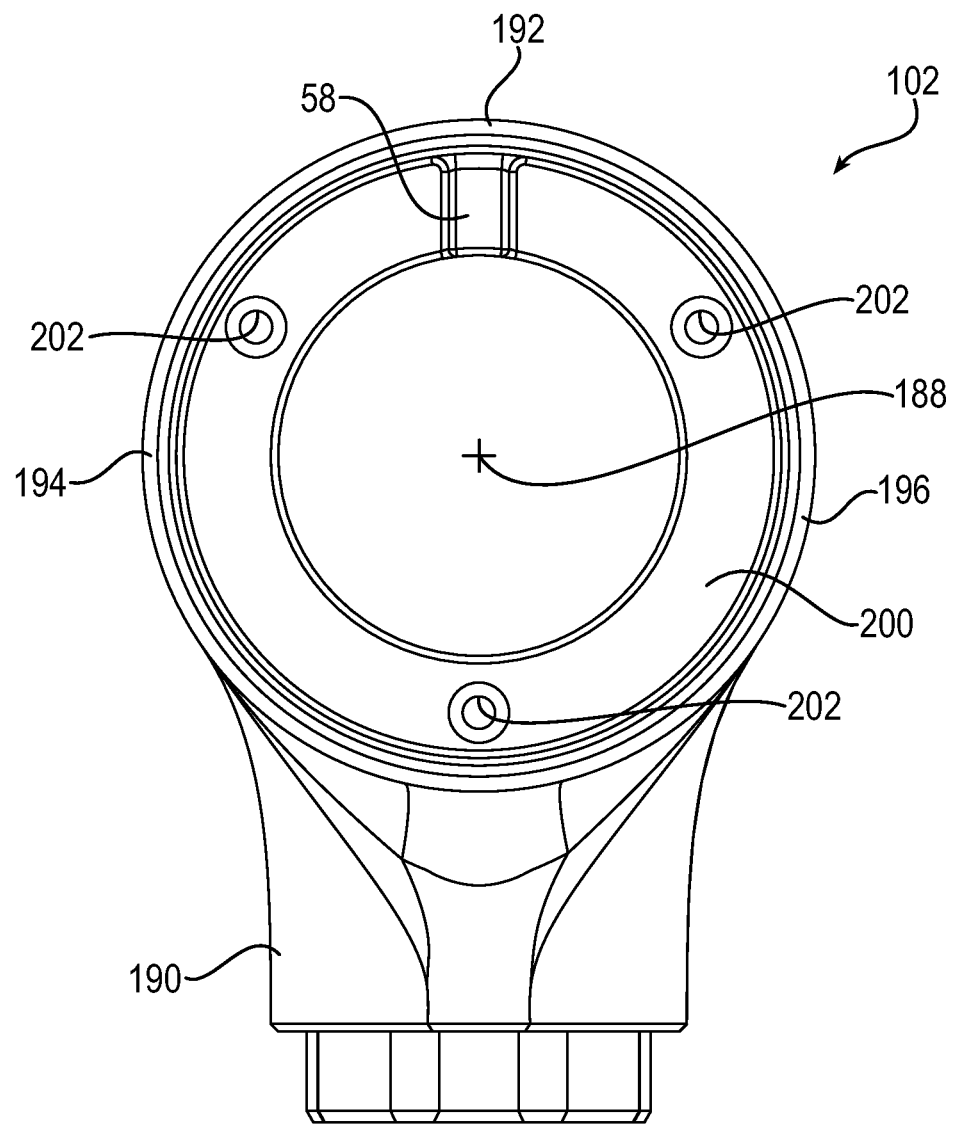
FIG. 7 is a bottom plan view of a knuckle joint housing of the FIG. 2 knuckle joint assembly.

The cartridge assembly receptacle 104 is formed as part of the knuckle joint housing 102. The knuckle joint housing 102 defines an opening 180 that has a vertical axis 188, which in FIG. 2 extends vertically and in FIG. 7 is perpendicular to the page. As shown in FIG. 2, the cartridge assembly 118 is removably insertable into the opening 180 so that the central axis 128 of the cartridge assembly 118 coincides with the vertical axis 188 of the knuckle joint housing 102. In this regard, "removably insertable" means the cartridge assembly 118 can be inserted in and removed from the cartridge assembly receptacle 104 of the knuckle joint housing 102. The cartridge assembly receptacle 104 is integral with a knuckle joint shoulder protrusion 190 of the knuckle joint housing 102. The knuckle joint shoulder protrusion 190 connects the knuckle joint housing 102 to an intermediate elongated portion 26 of the extension arm 16, in FIG. 1 located between the proximal hub 28 and the knuckle joint assembly 32. The cartridge assembly receptacle 104 includes a retaining clip clearance wall 192 and two laterally opposite side walls 194, 196 on laterally opposite sides of the retaining clip clearance wall 192. As its name suggests, the retaining clip clearance wall 192 is sufficiently low to allow the retaining clip 140 to clear the retaining clip clearance wall 192, that is, for the retaining clip 140 to move beyond the retaining clip clearance wall 192 when being moved between its engaged position and disengaged position. The cartridge assembly receptacle 104 also includes a flange 200 at the bottom of the opening 180. The flange 200 supports the cartridge assembly 118 in an axial position. As shown in FIG. 7, the flange 200 is circular in shape. The walls 192, 194, 196 of the cartridge assembly receptacle 104 project upwardly from the flange 200.

Figure 5:
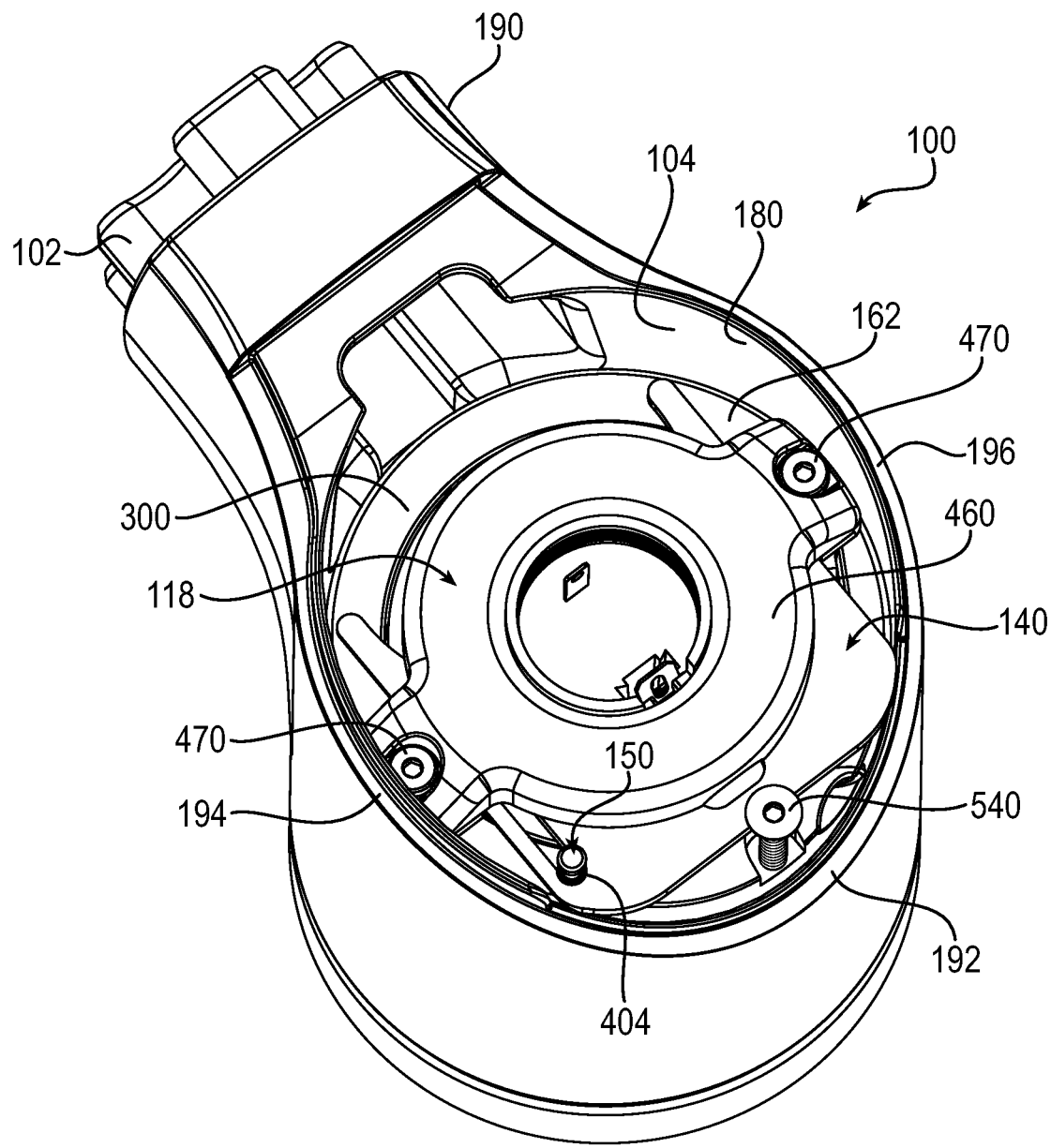
FIG. 5 is a top perspective view of the FIG. 2 knuckle joint assembly with a knuckle joint housing cover removed to show underlying components in greater detail.
Figure 6:
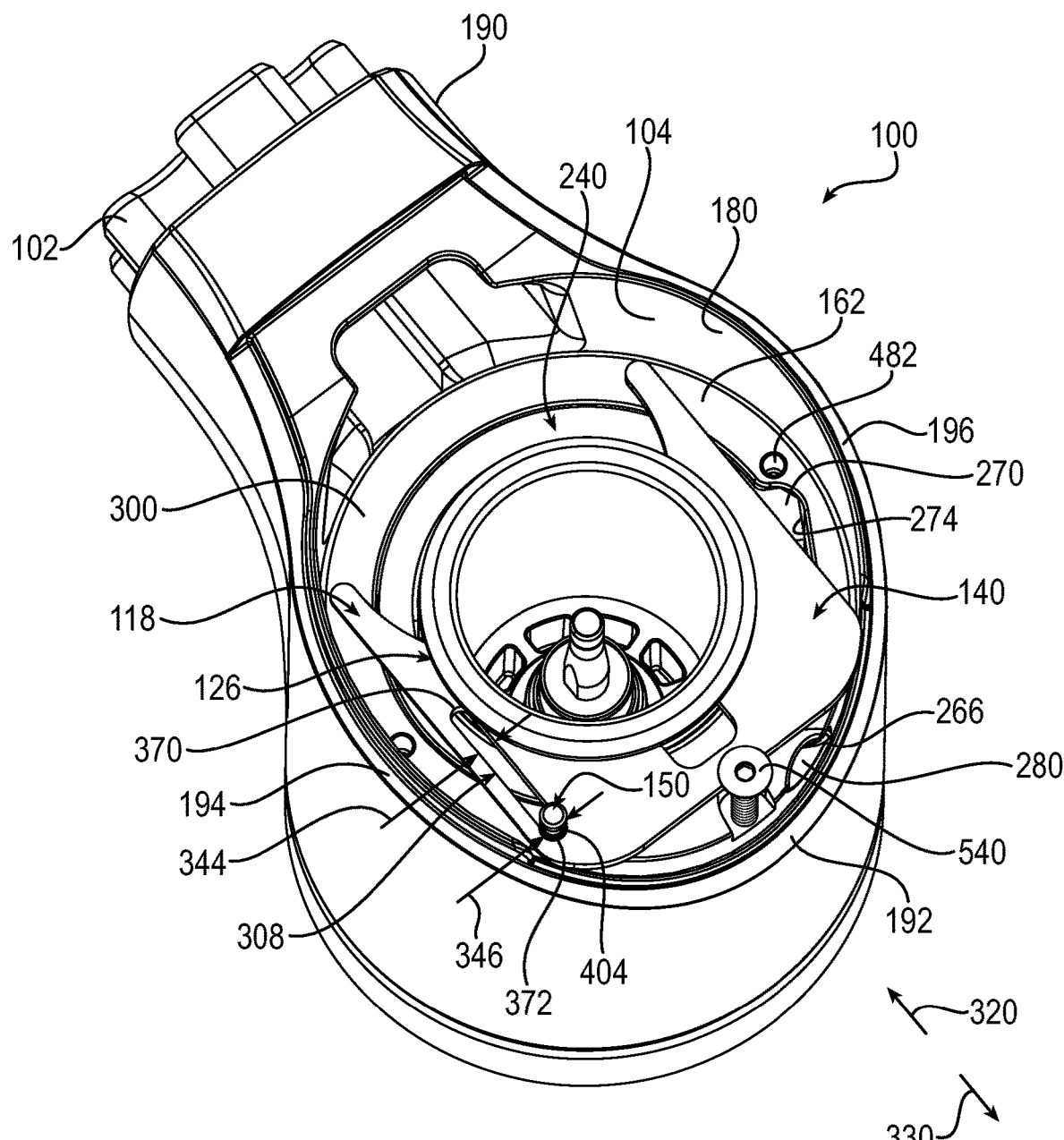
FIG. 6 is a top perspective view of the FIG. 2 knuckle joint assembly with a knuckle joint housing cover and combination female slip ring holder and retaining clip guide removed to show underlying components in greater detail.

In the illustrative embodiment, the opening 180 of the cartridge assembly receptacle 104 opens vertically upward and the cartridge assembly 118 is removably insertable vertically into the opening 180 along the vertical axis 188 where it can then be placed on the flange 200. As shown in FIGS. 2, 5 and 6, this is facilitated by the opening 180 in the knuckle joint housing 102 being larger than an outer perimeter of the cartridge assembly 118 when viewed vertically downward from the top. As will be appreciated, the opening 180 alternately, or additionally, could open horizontally outwardly. The opening 180 in the knuckle joint housing 102 could be larger than the side profile of the cartridge assembly 118 when viewed horizontally for example from the right side in FIG. 2; in which case, the cartridge assembly 118 could then be horizontally removably insertable into the opening 180 where it can then be situated on the flange 200. Of course, the opening 118 need not be larger in top view or side view than the respective top and side view profiles of the cartridge assembly 118, and other embodiments are contemplated. For example, the opening 118 could be sized such that the cartridge assembly 118 is removably insertable at an angle relative to vertical and horizontal before being positioned on the flange 200.

The cartridge housing 162 of the cartridge assembly 118 is configured to be fastened to the flange 200 of the cartridge assembly receptacle 104. As shown in FIGS. 2 and 7, the flange 200 includes a plurality of fastener through holes 202, three in the illustrative embodiment. As shown in FIGS. 2 and 9, a base 210 of the cartridge housing 162 includes a plurality of threaded openings 212, three in the illustrative embodiment, that axially align with the plurality of fastener through holes 202 in the flange 200 when the cartridge assembly 118 is inserted in the cartridge assembly receptacle 104. The cartridge housing 162 is fastened to the flange 200 via fasteners 216 passing through the through holes 202 in the flange 200 and engaging the respective threaded openings 212 in the base 210 of the cartridge housing 162.

Referring to FIGS. 1, 2, 5 and 6, in the fastened state the cartridge assembly 118 is positioned in the knuckle joint housing 102 such that movement of the retaining clip 140 between its disengaged position and engaged position is along an axis projecting radially outward from the central shaft or support column 14, or substantially in line with the intermediate elongated portion 26 of the extension arm 16. Other embodiments are contemplated. For example, the cartridge assembly 118 may be positioned in the knuckle joint housing 102 such that movement of the retaining clip 140 between its disengaged position and engaged position is along an axis perpendicular to an axis radially outward from the central shaft or support column 14, or perpendicular to the intermediate elongated portion 26 of the extension arm 16. To facilitate this, a corresponding one of laterally opposite side walls 194, 196 of the cartridge assembly receptacle 104 would be sufficiently low to allow the retaining clip 140 to clear the side wall 194, 196, that is, for the retaining clip 140 to move beyond the side wall 194, 196 when being moved between its disengaged position and engaged position.

In the illustrative embodiment, the through holes 192 and threaded openings 194 are equally angularly spaced apart, that is, by 120 degrees. It will be appreciated that the location, number and relative spacing of the through holes 192 and threaded openings 194 need not be limited to that which is shown, and other embodiments are contemplated. For example, the through holes 192 could be in one or more of the walls 192, 194, 196 of the cartridge assembly receptacle 104, and the threaded openings 194 could be in an outer wall of the cartridge housing 162. The number of through holes 192 and threaded openings 194 could be two angularly spaced by 180 degrees, or four angularly spaced by 90 degrees, etc. Further, the number of through holes 192 could be greater than the number of threaded openings 194, or vice versa, for example where it is desirable to provide redundancy or greater flexibility in the number of angular mounting positions for the cartridge assembly 118 in the cartridge assembly receptacle 104.

The cartridge assembly 118 may be equipped with a brake assembly 240 including at least one brake pad 242, two in the illustrated embodiment, selectively movable radially inward and radially outward relative to the central axis 128. Referring to FIG. 2, it will be appreciated that moving the brake pad 242 is movable radially inward and radially outward to respectively increase and decrease a frictional braking force to the spindle 126 rotatably supported by the rotary bearings 176, 178. The brake assembly 240 shown in FIGS. 2-4 and 6 is of the C clamp type and includes first and second arc shape brake pads 242. The clamp type brake assembly may alternatively be a split clamp type brake assembly as described in U.S. patent application Ser. No. 16/517,703, filed Jul. 22, 2019, and titled "Brake Assembly for Medical Device Support System," and may include snap fit brake pads as described in U.S. patent application Ser. No. 16/517,704, filed Jul. 22, 2019, and titled "Brake Assembly for Medical Device Support System," which are incorporated by reference for all purposes as if fully set forth herein. As shown in FIGS. 2-4, the cartridge assembly 118 arranges the C clamp brake assembly 240 axially, that is vertically, above the rotary bearings 176, 178. The C clamp brake assembly 240 may be cradled in a recess 244 of the cartridge housing 162, which in the illustrated embodiment is defined by a flange 256 projecting radially inwardly from a second bore 258 of the cartridge housing 162. As shown in FIGS. 2 and 3, the brake assembly 240 is axially supported by the flange 256.

Referring to FIG. 2, it will be appreciated that moving the first and second arc shape brake pads 242 of the brake assembly 240 toward and away from each other respectively increases and decreases a frictional braking force to the spindle 126 rotatably supported by the rotary bearings 176, 178. In contrast to a single brake pad applying a frictional braking force to one side of the spindle 126, the arc shape brake pads 242 apply a frictional braking force to two opposite sides of the spindle 126.

An actuator 266 such as a set screw may be used to selectively move the brake pad 242 radially inward and radially outward relative to the central axis 128 to respectively increase and decrease a frictional braking force to the spindle 126. In the case of the illustrated C clamp type brake assembly 240, the actuator 266 applies a clamping force against respective tabs 270 protruding radially outwardly relative to the central axis 128 and into a radially protruding notch 274 in the cartridge housing 162. As the actuator 266 moves the tabs 270 toward and away from each other, the tabs 270 urge the brake pads 242 toward and away from each other to respectively increase and decrease a frictional braking force to the spindle 126 therebetween. Referring to FIGS. 4 and 8, the actuator 266 is accessible from an opening 280 in an outer surface 282 of the cartridge housing 162. Examples of a suitable actuators are described in the afore mentioned patent applications, U.S. patent application Ser. Nos. 16/517,703 and 16/517,704 as well as in U.S. patent application Ser. No. 16/517,707, filed Jul. 22, 2019, and titled Brake Actuator for Medical Device Support System, which are incorporated by reference for all purposes as if fully set forth herein.

Figure 10:
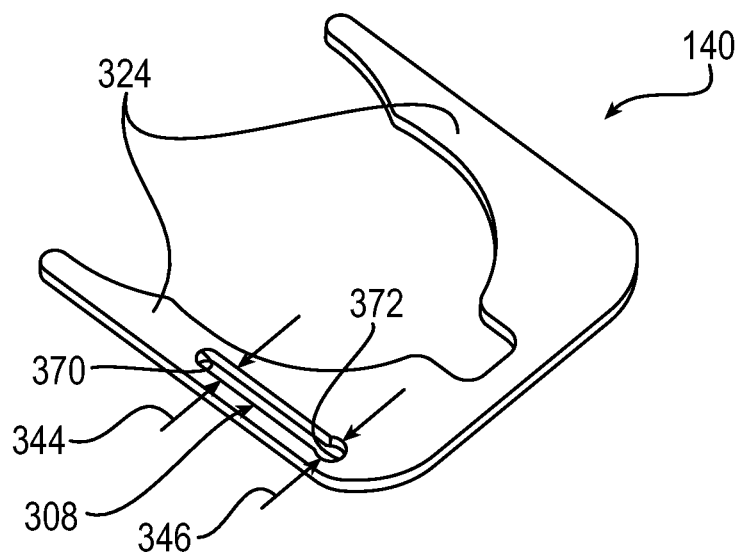
FIG. 10 is a top perspective view of a retaining clip of the FIG. 3 cartridge assembly.
Figure 11:
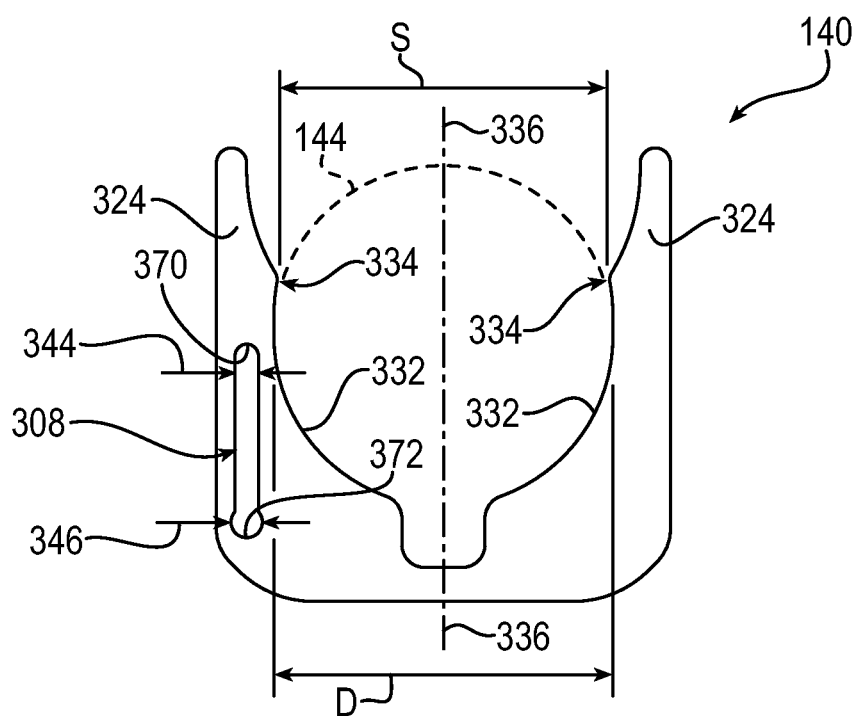
FIG. 11 is a top plan view of the FIG. 10 retaining clip.

FIGS. 2-6, 10 and 11 show the retaining clip 140 in greater detail. The retaining clip 140 is supported by an upper surface 300, in the illustrative embodiment the top surface, of the cartridge housing 162 of the cartridge assembly 118. The retaining clip 140 is selectively movable between a spindle disengaged position and a spindle engaged position and is constrained in this movement by a cooperative relationship between a slot 308 in the retaining clip 140 and the retaining pin 150, as will be described in greater detail further below. The retaining clip 140 is movable in a first direction 320 radially toward the central axis 128, to the left in FIGS. 3 and 6, to slidably engage the groove 144 in the spindle 126. As shown in FIGS. 6, 10 and 11, the illustrative retaining clip 140 has two prongs 324 that straddle the spindle 126 at two different angular positions around the spindle 126. The retaining clip 140 is movable in a second direction 330 radially away from the central axis 128, to the right in FIGS. 3 and 6, to disengage the groove 144 in the spindle 126. As will be appreciated, there normally will be multiple disengaged positions since the retaining clip 140 ordinarily will move beyond the precise location where its prongs 324 release the spindle 126, for example, to provide visible feedback to a technician that the retaining clip 140 has indeed released the spindle 126. As used herein, disengaged position refers to one or more disengaged positions.

Referring again to FIG. 11, the prongs 324 of the retaining clip 140 have respective arc portions 332 that have radii smaller than the radius of the spindle 126 and slightly larger than the radius of the groove 144 in the spindle 126, and respective inward curved portions 334 extending from the respective arc portions 332 that curve slightly inward toward a centerline 336 of the retaining clip 140 such that the lateral spacing S between the curved portions 334 is less than the diameter D of the groove 144 in the spindle 126. The narrower distance S between the curved portions 334 relative to the diameter D of the groove 144 in addition to friction forces that the retaining clip 140 incurs with the surfaces surrounding the retaining clip 140 together retain the retaining clip 140 in engagement with the groove 144 of the spindle 126. The prongs 324 of the retaining clip 144 are configured to flexibly expand during installation and removal. Thus, as the retaining clip 140 is moved in the first direction 320 (to the left in FIGS. 3 and 6) toward engagement with the groove 144 in the spindle 126, the curved portions 334, owing to their lateral spacing S being less than the diameter D of the groove 144, contact the groove 144 wall, causing the curved portions 334 to flexibly urge apart. As the retaining clip 140 is urged further in the first direction 320 (to the left in FIGS. 3 and 6) such that the curved portions 334 move beyond the midpoint of the diameter D of the groove 144, the curved portions 334 gradually return, or "snap back," to their unflexed position shown in FIG. 11. Thus, the retaining clip 140 is retained in the groove 144 both by frictionally engaging the surrounding surfaces that support and guide the retaining clip 140 and by the inward curved portions 334 of the two prongs 324 of the retaining clip 140 retaining clip engagement with the groove 144 of the spindle 126. The curved portions 334 of the retaining clip 140 are configured to prevent the retaining clip 140 from coming off the spindle 126 or more specifically out of the spindle groove 144 of the spindle 126 (to the right in FIGS. 3 and 6) during operation.

As shown in FIGS. 2, 5 and 6, the retaining clip 140 slidably engages the groove 144 in the spindle 126 to support the spindle 126 in an axial position along the central axis 128. Conversely, when the retaining clip 140 is disengaged from the groove 144, the retaining clip 140 releases the spindle 126 to allow movement of the spindle 126 along the central axis 128, and thus removal of the spindle 126 from the knuckle joint assembly 100. Referring to FIG. 1, release of the spindle 126 allows the load balancing arm 18 of which the spindle 126 is a part to be removed from the extension arm 16 of which the knuckle joint assembly 100 is a part.

FIGS. 10 and 11 show the slot 308 into which the retaining pin 150 projects. In general, the slot 308 has a relatively narrower width 344 and a relatively larger width 346. In the illustrative embodiment, the slot 308 has a keyhole shape wherein a narrower portion of the keyhole corresponds to the narrower width 344 of the slot 308 and a round portion of the keyhole corresponds to the larger width 346 of the slot 308. As will be appreciated, other shapes and types of slots are contemplated, such as square shape slots, open cutouts from the edge of the retaining clip 140, among others.

The retaining pin 150 is movable within the slot 308 in a direction transverse to a plane in which the retaining clip 140 and the slot 308 lie. The retaining pin 150 is movable up and down within the slot 308 between a first position and a second position, or a vertically lower position and a vertically upper position in the illustrative embodiment. In the first position, the retaining pin 150 has a width 360 that allows movement of the retaining clip 140 between the spindle engaged position and the spindle disengaged position but prevents removal of the retaining clip 140 from the cartridge assembly 118. As the retaining clip 140 is moved, the retaining pin 150 slides within the slot 308, in the illustrative embodiment between one end 370 of the slot 308 and an opposite end 372 of the slot 308. In the second position, shown in FIGS. 3, 5 and 6, the retaining pin 150 has a width 380 that blocks movement of the retaining clip 140 from the spindle engaged position.

Accordingly, the retaining clip 140 is selectively movable based on the width 344, 346 of the slot 308 and whether the retaining pin 150 is in the first position with its first width 360 in the plane of the retaining clip 140 or in the second position with its second width 380 in the plane of the retaining clip 140. In the first position, the retaining pin 150 has a width 360 that is less than the narrower width slot 344 so that the retaining pin 150 slides within the slot 308 as the retaining clip 140 is moved between radially toward and radially away from the central axis 128, that is between the spindle engaged position and the spindle disengaged position. In the second position, the retaining pin 150 has a width 380 that is greater than the narrower width slot 344 so that the retaining pin 150 is unable to slide from the larger width slot 346 to the narrower width slot 344, which blocks movement of the retaining clip 140 from the spindle engaged position.

Referring to FIGS. 3, 4, 8 and 9, the illustrative retaining pin 150 has a pin axis 400 and a minor outside diameter (OD) 402 and a major outside diameter (OD) 404 at different positions along the pin axis 400 that correspond respectively to the afore described first and second widths 360, 380 at the respective first and second positions of the retaining pin 150. The retaining pin 150 is mounted within a hole 420 in the cartridge housing 162 for reciprocable movement between the first position and the second position. In the illustrative embodiment, the hole 420 has a central axis 428 that is parallel to the central axis 128 of the bore 164 of the cartridge housing 162. The retaining pin 150 is spring biased by a biasing member 434 toward the second position, that is, to the vertically upper position. The biasing member 434 may be a coil spring as illustrated or any other suitable member that biases the retaining pin 150 upward. The retaining pin 150 is bound for reciprocable movement beyond the second position by a ledge 446 inside the hole 420. The retaining pin 150 is bound for reciprocable movement beyond the first position by a set screw 450 inside the hole 420.

Thus, for example, referring again to FIG. 3, when the retaining pin 150 is pushed down to where the relatively narrower width 360 (or minor OD 402 in the present example) of the retaining pin 150 is vertically aligned with the retaining clip 140, that is the first position in the illustrative embodiment, then the bottom surface of the retaining pin 150 contacts the top of the set screw 450, stopping further movement of the retaining pin 150 beyond the first position, and allowing the retaining clip 140 to be disengaged from the spindle groove 144 but preventing the retaining clip 140 from being removed from the knuckle joint assembly 100. In some embodiments, the retaining pin 150 may be sized such that the retaining pin 150 can be pushed down even further until blocked by the set screw 450, for example, such that a top wide portion of the retaining pin 150 is vertically aligned with the retaining clip 140, preventing the retaining clip 140 from being disengaged from the spindle groove 144. In any event, the retaining pin 150 is moveable between a first position in which the retaining pin 150 allows the retaining clip 140 to be disengaged from the spindle 126 but not removed and a second position in which the retaining pin 150 locks the clip in the spindle-engaged position.

Referring more closely to FIG. 6, when the retaining clip 140 slidably engages the groove 144 in the spindle 126, the larger width slot 346, or the round portion of the keyhole slot, vertically aligns with the retaining pin 150. Because the retaining pin 150 is biased to the second position, that is, to the vertically upper position, the relatively wider width 380 of the retaining pin 150, or the major OD 404, snaps into the larger width slot 346 automatically. Thus, the retaining clip 140 and biased retaining pin 150 provide a self-locking feature and a visible and tactile feedback to the technician that the retaining clip 140 has indeed slidably engaged the groove 144 in the spindle 126. Similarly, when it is desired to disengage the retaining clip 140 from the groove 144 in the spindle 126 to release the spindle 126 from the knuckle joint assembly 100, the retaining pin 150 must be pressed down against the upward biasing force exerted by the biasing member 434. Thus, the technician must affirmatively press down the retaining pin 150 to enable the retaining clip 140 to be slid away from the central axis 128 to disengage the groove 144 in the spindle 126.

Figure 12:
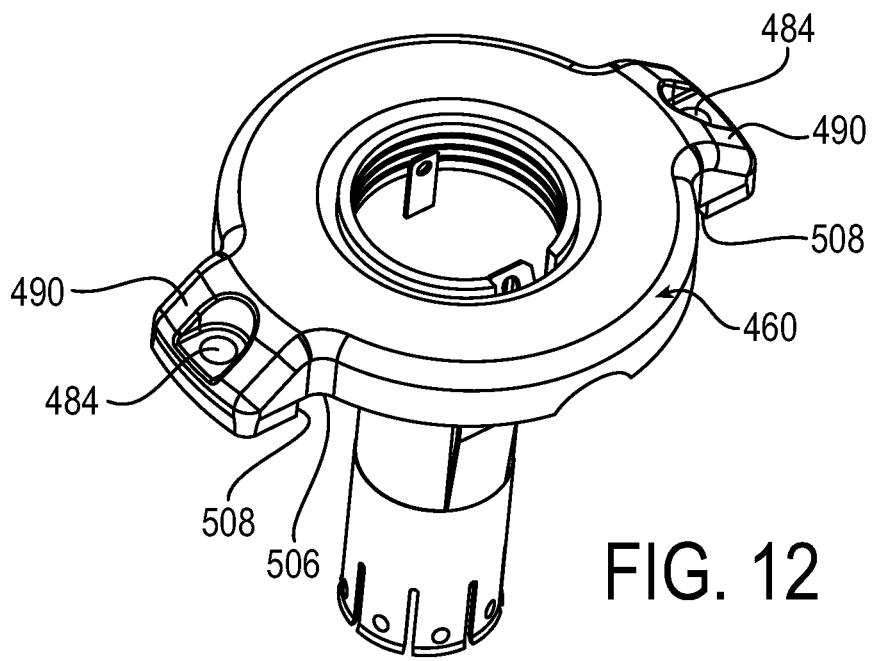
FIG. 12 is a top perspective view of a combination female slip ring holder and retaining clip guide of the FIG. 3 cartridge assembly.
Figure 13:
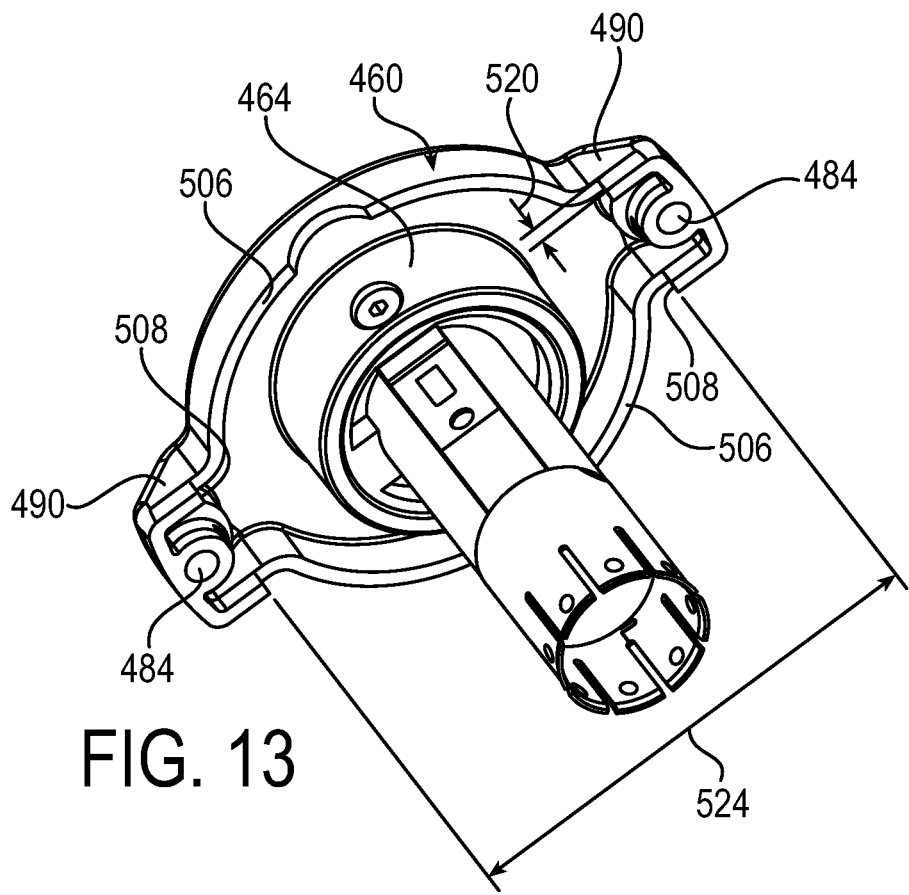
FIG. 13 is a bottom perspective view of a combination female slip ring holder and retaining clip guide of the FIG. 3 cartridge assembly.

Turning now to FIGS. 12 and 13, there is shown a combined retaining clip guide 460 and female slip ring holder 464 of the cartridge assembly 118. In the illustrative embodiment, the retaining clip guide 460 and female slip ring holder 464 are a single integral component and have a generally annular shape in top plan view. As shown in FIGS. 4, 5, 8 and 9, the retaining clip guide 460 is fastened to the upper surface 300 of the cartridge housing 162 via fasteners 470. The upper surface 300 of the cartridge housing 162 includes a pair of threaded openings 482 that axially align with a pair of fastener through holes 484 in respective laterally opposite flanges 490 of the retaining clip guide 460 when the retaining clip guide 460 is positioned on the upper surface 300 of the cartridge housing 162, where laterally opposite in this regard means laterally opposite sides of a central axis of the retaining clip guide 460 or diametrically opposite sides of the retaining clip guide 460. The retaining clip guide 460 is fastened to the upper surface 300 via the fasteners 470 passing through the through holes 484 in the flanges 490 and engaging the respective threaded openings 482 in the upper surface 300 of the cartridge housing 162.

The retaining clip guide 460 defines two motion restraining guide surfaces relative to the retaining clip 140, an upper guide surface 506 and laterally opposite guide surfaces 508, both of which are integrated in the lower structure of the retaining clip guide 460. With the retaining clip guide 460 fastened to the cartridge housing 162, the upper guide surface 506 and the upper surface 300 of the cartridge housing 162 form a gap 520, the height of which is slightly greater than the height of the retaining clip 140 to provide a slidable fit for the retaining clip 140. The laterally opposite guide surfaces 508 are formed by the flanges 490 and project vertically downward from the upper guide surface 506. The spacing between the laterally opposite guide surfaces 508 forms a gap 524, the width of which is slightly greater than the width of the retaining clip 140 to provide a slidable fit for the retaining clip 140. In operation, the guide surfaces 506, 508 restrain movement of the retaining clip 140 in two axes of motion. The upper guide surface 506 restrains vertical motion and the laterally opposite guide surfaces 508 restrain side to side motion. In the illustrative embodiment, the laterally opposite guide surfaces 508 run parallel to the slot 308 in the retaining clip 140. In this way, the laterally opposite guide surfaces 508 restrain side to side motion of the retaining clip 140 so that the retaining clip 140 moves along the direction of the slot 308.

In operation, the laterally opposite guide surfaces 508 prevent excessive radial motion of the retaining clip 140, which also helps prevent the retaining clip 140 from working its way off the spindle groove 144.

The female slip ring holder 464 is fastened to the upper surface 300 of the cartridge housing 162 through the retaining clip guide 460. As shown in FIGS. 2 and 3, the female slip ring holder 464 is adapted to hold a female slip ring in concentric relation to the central axis 128 of the cartridge assembly 118. In the illustrative embodiment, the female slip ring holder 464 and the retaining clip guide 460 are coupled together to constitute a single combined component. As will be appreciated, the retaining clip guide 460 could be constructed without the female slip ring holder 464, for example to accommodate a continuous cable run application. As shown in FIG. 4, the retaining clip guide 460 can also or alternately provide a central pass through hole 526 to route a cable run along the central axis 128.

It will further be appreciated that the retaining clip guide 460 can be equipped without any electrical connection capabilities and merely function as a retaining clip guide 460. In some applications, the retaining clip guide 460 itself may be omitted. In still further applications, the female slip ring holder 464, or a cable holder, may be provided, having the same mounting structure as the retaining clip guide 460 but without the guide surfaces 506, 508.

Referring again to FIG. 2, the knuckle joint assembly 100 includes a knuckle joint housing cover 528. The knuckle joint housing cover 528 covers the opening 180 in the cartridge assembly receptacle 104 of the knuckle joint assembly 100. As shown in FIG. 1, at one end, the knuckle joint housing cover 528 has a groove 530 that receives a corresponding size tab or tongue 532 in the knuckle joint housing 102 at the edge of the opening 180. At an opposite end, the knuckle joint housing cover 528 is fastened to the upper surface 300 of the cartridge housing 162 via a fastener 540. As shown in FIGS. 4-6 and 8, the upper surface 300 of the cartridge housing 162 includes a threaded opening 542 that axially aligns with a fastener through hole 544 in the knuckle joint housing cover 528 when the knuckle joint housing cover 528 is mounted on an upper edge of the walls 192, 194, 196 of the cartridge assembly receptacle 104 portion of the knuckle joint housing 102. The knuckle joint housing cover 528 is fastened to the cartridge housing 162 via the fasteners 540 passing through the through hole 544 in the knuckle joint housing cover 528 and engaging the respective threaded opening 542 in the upper surface 300 of the cartridge housing 162.

Referring to FIGS. 2, 5 and 6, the path of movement of the retaining clip 140 relative to the knuckle joint housing 102 is such that the knuckle joint housing cover 528 cannot be installed onto the knuckle joint housing 102 in the case where the retaining clip 140 is not slidably engaged in the groove 144 of the spindle 126. In other words, if the retaining clip 140 is withdrawn from the groove 144, that is, to a disengaged position, then the retaining clip 140 projects beyond the retaining clip clearance wall 192 (to the bottom right of FIG. 5) into the path of installation of the knuckle joint housing cover 528 onto the knuckle joint housing 102.

It will be appreciated that the cartridge assembly 118 contains multiple functionality and simplifies serviceability. The cartridge assembly 118 equipped with rotary bearings 176, 178, brake assembly 240, retaining clip 140, retaining pin 150, retaining clip guide 460, and electrical connection capabilities, allows for plug-n-play connection of load balancing arms 18 with minimal effort. The cartridge assembly 118 includes a cartridge housing 162 with rotary bearings 176, 178 fitted therein to rotatably support the spindle 126, and is removably insertable into the knuckle joint housing 102 for simplified servicing or replacement without for example having to disassemble and return an entire extension arm 16 or medical device support system 10 to the manufacturer or supplier.

It will also be appreciated that the knuckle joint assembly 100 has multiple safety mechanisms. When the retaining clip 140 is slidably engaged in the groove 144 in the spindle 126, the biased retaining pin 150 automatically snaps upward to lock the retaining clip 140 in place. To disengage the retaining clip 140 from the spindle 126, the biased retaining pin 150 must affirmatively be pressed down to enable the retaining clip 140 to be withdrawn. The retaining clip 140 cannot be removed entirely from the knuckle joint assembly 100 since the retaining pin 150 prevents such removal when it abuts the end 370 of the slot 308. As the retaining clip 140 cannot be removed from the cartridge assembly 118, the retaining clip 140 cannot be misplaced or reinserted in an incorrect orientation. If the retaining clip 140 is not in the spindle engaged position the knuckle joint housing cover 528 cannot be installed on the knuckle joint housing 102.

Figure 14:
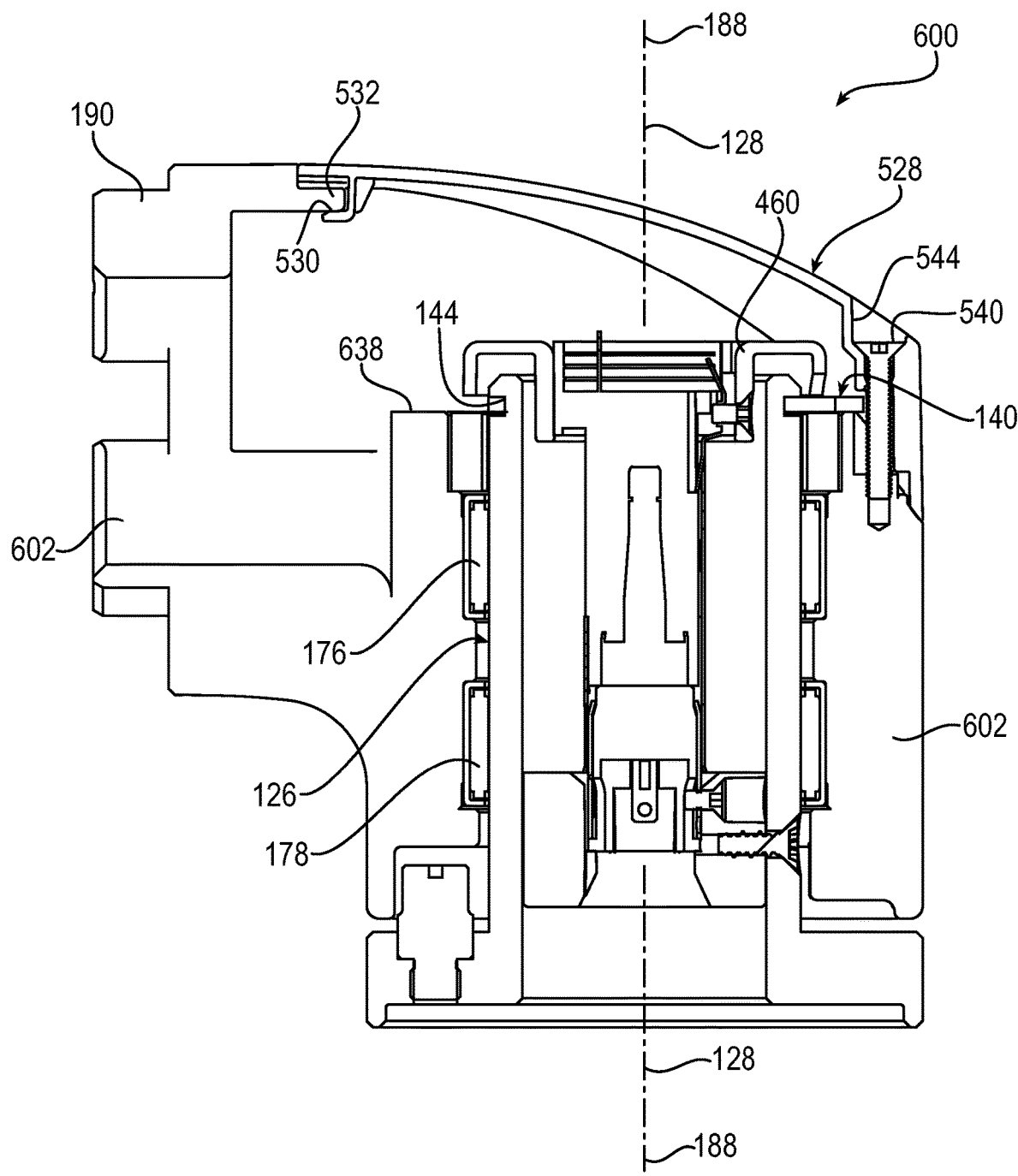
FIG. 14 is a side cross section view of a knuckle joint assembly in accordance with another embodiment of the invention.
Figure 15:
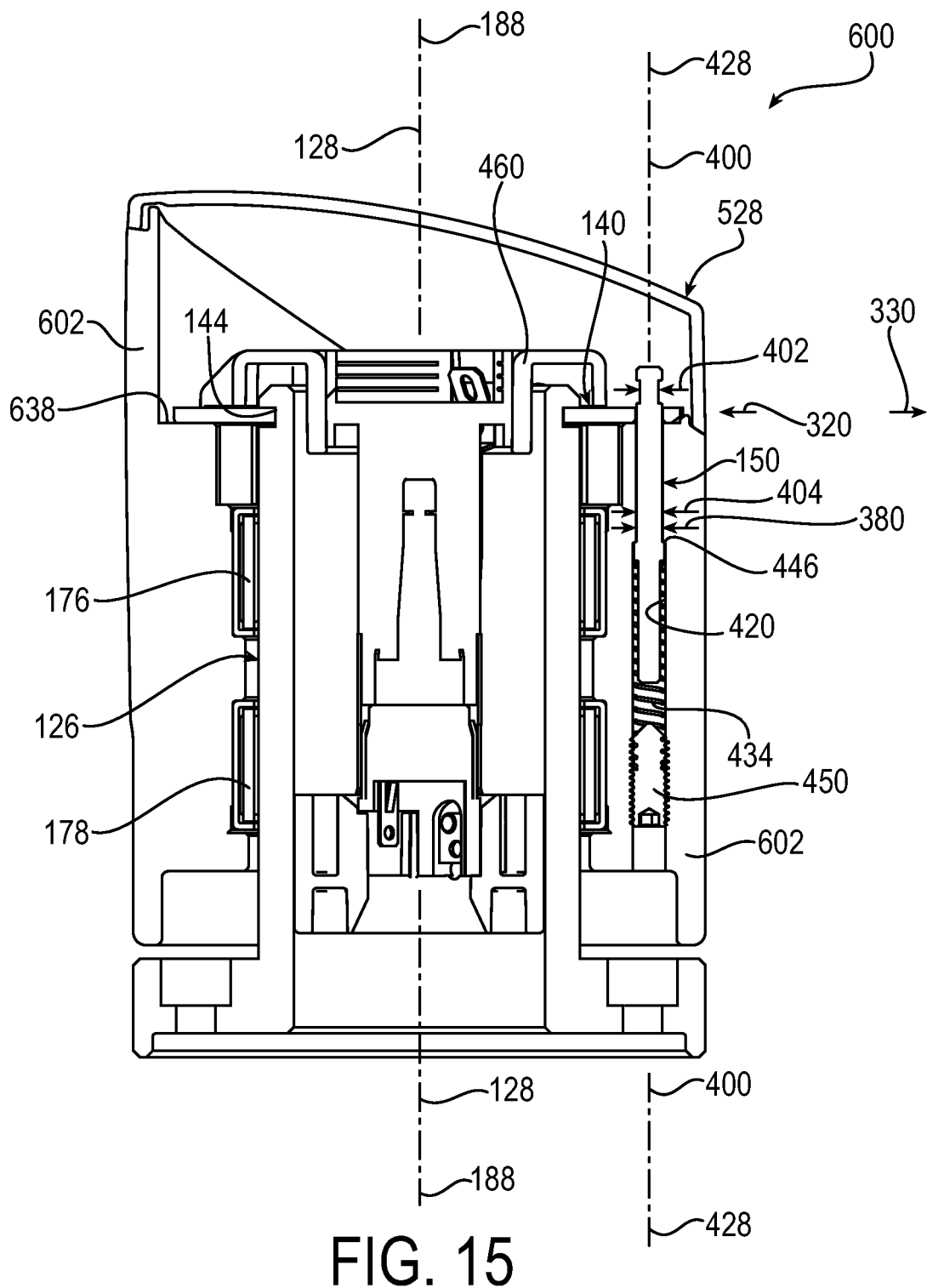
FIG. 15 is a side cross section view of the FIG. 14 knuckle joint assembly, showing a retaining pin of the knuckle joint assembly.

FIGS. 14 and 15 show a knuckle joint assembly 600 according to another embodiment of the invention. The knuckle joint assembly 600 is in many respects similar to the above-referenced knuckle joint assembly 100, and consequently the same reference numerals are used to denote structures corresponding to similar structures in the knuckle joint assembly 100. In addition, the foregoing description of the knuckle joint assembly 100 is equally applicable to the knuckle joint assembly 600 except as noted below. Moreover, it will be appreciated upon reading and understanding the specification that aspects of the knuckle joint assemblies 100, 600 may be substituted for one another or used in conjunction with one another where applicable.

The knuckle joint assembly 600 includes a knuckle joint housing 602 including one or more rotary bearings 176, 178 having a central axis 128 and configured to receive axially therethrough a spindle 126 to rotatably support the spindle 126 about the central axis 128. A retaining clip 140 is selectively movable between a disengaged position in which the retaining clip 140 is disengaged from a groove 144 in the spindle 126 to allow movement of the spindle 126 along the central axis 128, and an engaged position in which the retaining clip 140 slidably engages the groove 144 in the spindle 126 to support the spindle 126 in an axial position along the central axis 128. A retaining pin 150 is movable between a first position in which the retaining pin 150 allows movement of the retaining clip 140 between the disengaged position and the engaged position but prevents removal of the retaining clip 140 from the knuckle joint assembly 600, and a second position in which the retaining pin 150 blocks movement of the retaining clip 140 from the engaged position.

The retaining clip 140 may be supported by an upper surface 638 of the knuckle joint housing 602. The retaining clip 140 is movable in a first direction 320 radially toward the central axis 128, to the left in FIG. 15, to slidably engage the groove 144 in the spindle 126, and in a second direction 330 radially away from the central axis 128, to the right in FIG. 15, to disengage the groove 144 in the spindle 126.

The retaining clip 140 has a slot 308 into which the retaining pin 150 projects. The slot 308 includes a relatively narrower width slot 344 and a relatively larger width slot 346. The retaining clip 140 is selectively movable based on the width of the slot 308 and whether the retaining pin 150 is in the first position or the second position. The illustrative slot 308 has a keyhole shape wherein a narrower portion of the keyhole corresponds to the narrower width 344 of the slot 308 and a round portion of the keyhole corresponds to the larger width 346 of the slot 308. The retaining pin 150 in the first position has a width 360 that is less than the narrower width slot 344 so that the retaining pin 150 slides within the slot 308 as the retaining clip 140 is moved between the disengaged position and the engaged position. The retaining pin 150 in the second position has a width 380 that is greater than the narrower width slot 344 so that the retaining pin 150 is unable to slide from the larger width slot 346 to the narrower width slot 344 which blocks movement of the retaining clip 140 from the engaged position.

The retaining pin 150 has a pin axis 400 and a minor OD 402 and a major OD 404 at different positions along the pin axis 400 that correspond respectively to the first position and second position. The retaining pin 150 is mounted within a hole 420 in the knuckle joint housing 602 for reciprocable movement between the first position and the second position. The hole 420 has a central axis 428 that is parallel to the central axis 128 of the rotary bearings 176, 178. The retaining pin 150 is spring biased toward the second position. The retaining pin 150 is bound for reciprocable movement beyond the second position by a ledge 446 inside the hole 420. The retaining pin 150 is bound for reciprocable movement beyond the first position by a set screw 450 inside the hole 420.

Thus, for example, referring again to FIG. 3, when the retaining pin 150 is pushed down to where the relatively narrower width 360 (or minor OD 402 in the present example) of the retaining pin 150 is vertically aligned with the retaining clip 140, that is the first position in the illustrative embodiment, then the bottom surface of the retaining pin 150 contacts the top of the set screw 450, stopping further movement of the retaining pin 150 beyond the first position, and allowing the retaining clip 140 to be disengaged from the spindle groove 144 but preventing the retaining clip 140 from being removed from the knuckle joint assembly 600. In some embodiments, the retaining pin 150 may be sized such that the retaining pin 150 can be pushed down even further until blocked by the set screw 450, for example, such that a top wide portion of the retaining pin 150 is vertically aligned with the retaining clip 140, preventing the retaining clip 140 from being disengaged from the spindle groove 144. In any event, the retaining pin 150 is moveable between a first position in which the retaining pin 150 allows the retaining clip 140 to be disengaged from the spindle 126 but not removed and a second position in which the retaining pin 150 locks the clip in the spindle-engaged position.

A retaining clip guide 460 is configured to restrain the retaining clip 140 in two axes of motion including vertical motion and side to side motion so that the retaining clip 140 moves along the direction of the slot 308.

A knuckle joint housing cover 528 is connectable to the knuckle joint housing 602 to cover the knuckle joint housing 602. When the retaining clip 140 is in a disengaged position the retaining clip 140 blocks the knuckle joint housing cover 528 from being connectable to the knuckle joint housing 602.

FIGS. 16-20 show a cartridge assembly 700 according to another embodiment of the invention. The cartridge assembly 700 is in many respects similar to the above-referenced cartridge assembly 118, and consequently the same reference numerals are used to denote structures corresponding to similar structures in the cartridge assembly 118. In addition, the foregoing description of the cartridge assembly 118 is equally applicable to the cartridge assembly 700 except as noted below. Moreover, it will be appreciated upon reading and understanding the specification that aspects of the cartridge assemblies 118, 700 may be substituted for one another or used in conjunction with one another where applicable.

Turning then to FIGS. 16-20, the cartridge assembly 700 includes a cartridge housing 708, upper and lower rotary bearings 176, 178 (see FIGS. 2-4 and 14-15) press fitted in the cartridge housing 708 in like manner as the afore described cartridge housing 162, the retaining clip 702, and a female slip ring holder 714. In a like manner as the afore described cartridge assembly 118, the cartridge assembly 700 is removably insertable in the cartridge assembly receptacle 104 of the knuckle joint housing 102 of the knuckle joint assembly 100 (see FIGS. 5 and 6). Also, in like manner as the cartridge assembly 118, the rotary bearings 176, 178 of the cartridge assembly 700 rotatably support a spindle 126, for example the spindle 24 of a respective load balancing arm 18 in FIG. 1, about a central axis 128 (see FIG. 2). Still further, in like manner as the retaining clip 140 of the cartridge assembly 118, a retaining clip 702 of the cartridge assembly 700 is movable between an engaged position to slidably engage the groove 144 in the spindle 126 to support the spindle 126 in an axial position along the central axis 128, and a disengaged position in which the retaining clip 702 is disengaged from the groove 144 to allow movement of the spindle 126 along the central axis 128 (see FIG. 2). The cartridge assembly 700 simplifies servicing or replacement of internal components of the knuckle joint assembly 100 without having to disassemble and return an entire extension arm 16 or medical device support system 10 (see FIG. 1) to a manufacturer or supplier.

Figure 16:
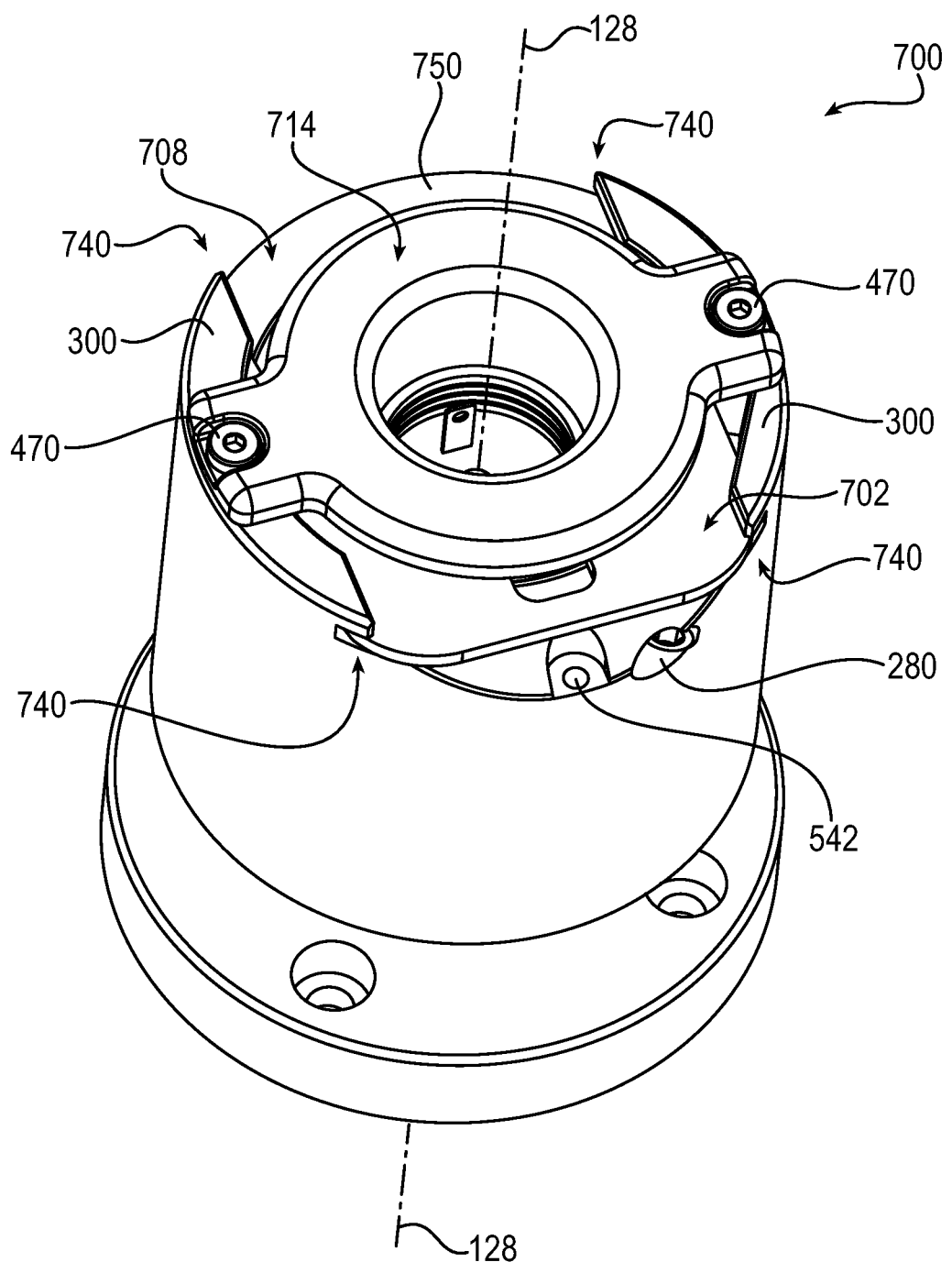
FIG. 16 is a top perspective view of a cartridge assembly in accordance with another embodiment of the invention.
Figure 17:
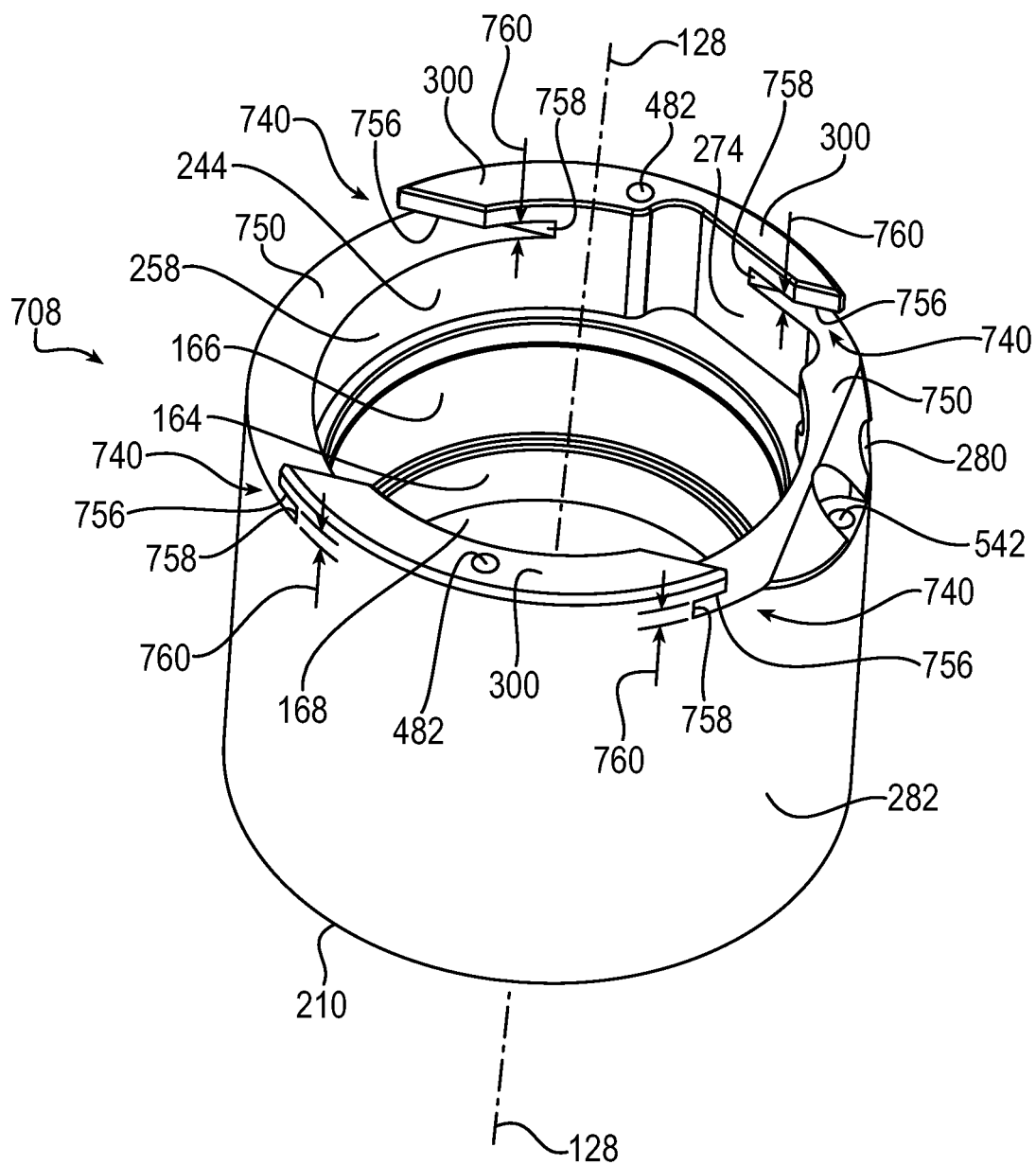
FIG. 17 is a top perspective view of a cartridge housing of the FIG. 16 cartridge assembly.
Figure 18:
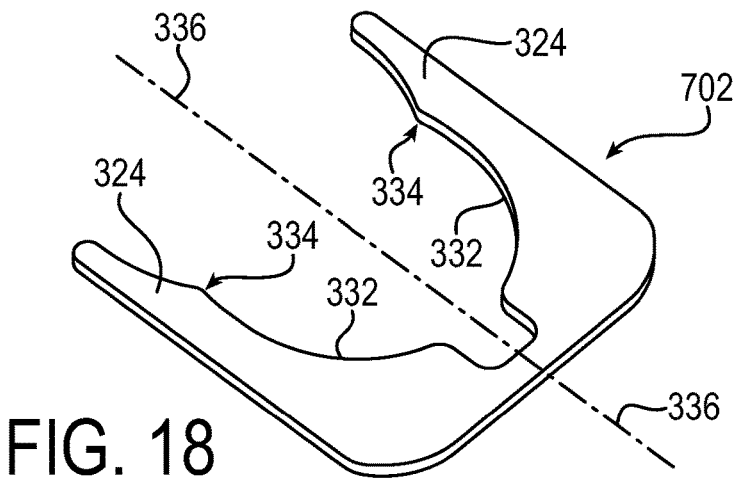
FIG. 18 is a top perspective view of a retaining clip of the FIG. 16 cartridge assembly.
Figure 19:
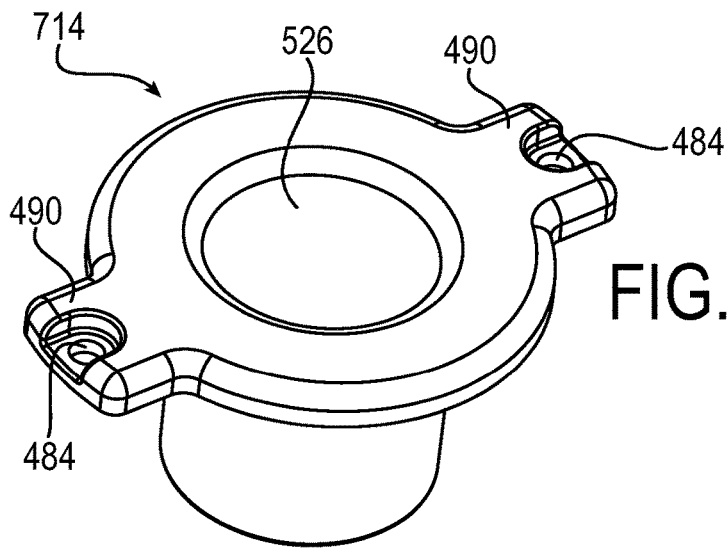
FIG. 19 is a top perspective view of a female slip ring holder of the FIG. 16 cartridge assembly.

FIGS. 16 and 18 show the retaining clip 702 in greater detail, and FIG. 19 shows the cartridge housing 708 in greater detail. The retaining clip 702 has two prongs 324 that straddle the spindle 126 at two different angular positions around the spindle 126 in the same manner as the afore described retaining clip 140. The retaining clip 702, however, is supported and guided by a radially protruding inverted T-shape slot 740 formed in an upper portion of the cartridge housing 708. In the illustrative embodiment, the radially protruding slot 740 includes an axially supporting lower surface 750 and two motion restraining guide surfaces 756, 758, which include laterally opposite upper guide surfaces 756 and laterally opposite side guide surfaces 758, where laterally opposite in this regard means laterally opposite sides of the central axis 128 of the cartridge housing 708 or diametrically opposite sides of the cartridge housing 708. The motion restraining guide surfaces 756, 758 may be integrated in the upper portion structure of the cartridge housing 708, for example as inverted L-shape projections or flanges projecting vertically upward from the axially supporting lower surface 750, as shown, or fastened to the axially supporting lower surface 750 or other surface of the cartridge housing 708. The axially supporting lower surface 750 and the laterally opposite upper guide surfaces 756 of the cartridge housing 700 form respective laterally opposite gaps 760, the heights of which are slightly greater than the height of the retaining clip 702 to provide a slidable fit for the retaining clip 702. The spacing between the laterally opposite side guide surfaces 758 forms a gap 764, the width of which is slightly greater than the width of the retaining clip 702 to provide a slidable fit for the retaining clip 702.

During installation of the retaining clip 702 into the radially protruding slot 740, and in operation, the laterally opposite guide surfaces 756, 758 restrain movement of the retaining clip 702 in two axes of motion. The laterally opposite upper guide surfaces 756 restrain vertical motion of the retaining clip 702 and the laterally opposite side guide surfaces 758 restrain side to side motion of the retaining clip 702. In operation, when the retaining clip 702 is slidably engaged in the groove 144 of the spindle 126, the axially supporting lower surface 750 axially supports the retaining clip 702 which, in turn, axially supports the spindle 126. Further, in operation, the retaining clip 702 is retained in the groove 144 both by frictionally engaging the walls 750, 756, 758 that form the slot 740 and, as with the afore described retaining clip 140 (see FIG. 11), by the inward curved portions 334 of the two prongs 324 of the retaining clip 140 retaining clip engagement with the groove 144 of the spindle 126. Also in operation, the inverted T-shape slot 740 prevents excessive radial motion of the retaining clip 702, which also helps prevent the retaining clip 702 from working its way off the spindle groove 144.

Figure 20:
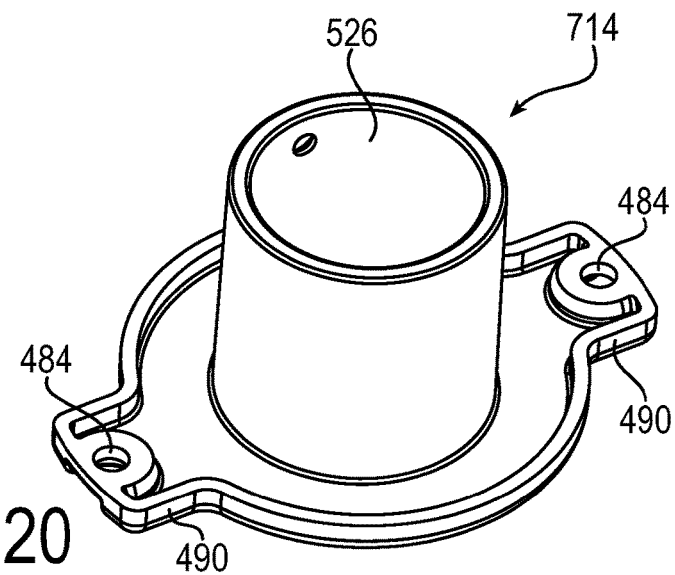
FIG. 20 is a bottom perspective view of the FIG. 19 female slip ring holder.

Turning now to FIGS. 19 and 20, there is shown greater detail of the female slip ring holder 714 of the cartridge assembly 700. The female slip ring holder 714 has a generally annular shape in top plan view. The female slip ring holder 714 is fastened to the upper surface 300 of the cartridge housing 708 via fasteners 470. The upper surface 300 of the cartridge housing 162 includes a pair of threaded openings 482 that axially align with a pair of fastener through holes 484 in respective laterally opposite flanges 490 of the female slip ring holder 714 when the female slip ring holder 714 is positioned on the upper surface 300 of the cartridge housing 708, where laterally opposite in this regard means laterally opposite sides of a central axis of the female slip ring holder 714 or diametrically opposite sides of the female slip ring holder 714. The female slip ring holder 714 is fastened to the upper surface 300 via the fasteners 470 passing through the through holes 484 in the flanges 490 and engaging the respective threaded openings 482 in the upper surface 300 of the cartridge housing 708. In like manner as the female slip ring holder 464 (see FIGS. 2-4), the female slip ring holder 714 is adapted to hold a female slip ring in concentric relation to the central axis 128 of the cartridge assembly 700. The female slip ring holder 714 can also or alternately provide a central pass through hole 526 to route a cable run along the central axis 128.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A knuckle joint assembly for a medical device support system, comprising:
a knuckle joint housing including a rotary bearing having a central axis and configured to receive axially therethrough a spindle to rotatably support the spindle about the central axis;
a retaining clip selectively movable between a disengaged position in which the retaining clip is disengaged from a groove in a spindle to allow movement of the spindle along the central axis, and an engaged position in which the retaining clip slidably engages the groove in the spindle to support the spindle in an axial position along the central axis; and,
a retaining pin movable between a first position in which the retaining pin allows movement of the retaining clip between the disengaged position and the engaged position but prevents removal of the retaining clip from the knuckle joint assembly, and a second position in which the retaining pin blocks movement of the retaining clip from the engaged position.

2. The knuckle joint assembly of claim 1, wherein the retaining clip is supported by an upper surface of the knuckle joint housing.

3. The knuckle joint assembly of claim 1, wherein the retaining clip is movable in a first direction radially toward the central axis to slidably engage a groove in a spindle, and in a second direction radially away from the central axis to disengage the groove in the spindle.

4. The knuckle joint assembly of claim 1, wherein the retaining clip is supported by a radially protruding slot in an upper portion of the knuckle joint housing.

5. The knuckle joint assembly of claim 4, wherein the radially protruding slot includes an axially supporting lower surface and laterally opposite upper guide surfaces that form respective laterally opposite gaps, wherein the heights of the gaps are greater than the height of the retaining clip to provide a slidable fit for the retaining clip.

6. The knuckle joint assembly of claim 4, wherein the radially protruding slot includes laterally opposite side guide surfaces that form a gap, the width of which is slightly greater than the width of the retaining clip to provide a slidable fit for the retaining clip.

7. The knuckle joint assembly of claim 1, wherein the retaining pin has a pin axis and a minor OD and a major OD at different positions along the pin axis that correspond respectively to the first position and second position.

8. The knuckle joint assembly of claim 1, wherein the retaining pin is mounted within a hole in the knuckle joint housing for reciprocable movement between the first position and the second position.

9. The knuckle joint assembly of claim 8, wherein the hole has a central axis that is parallel to the central axis of the rotary bearing.

10. The knuckle joint assembly of claim 8, wherein the retaining pin is spring biased toward the second position.

11. The knuckle joint assembly of claim 8, wherein the retaining pin is bound for reciprocable movement beyond the second position by a ledge inside the hole.

12. The knuckle joint assembly of claim 8, wherein the retaining pin is bound for reciprocable movement beyond the first position by a set screw inside the hole.

13. The knuckle joint assembly of claim 1, wherein the retaining clip has a slot into which the retaining pin projects, the slot having a relatively narrower width and a relatively larger width, and wherein the retaining clip is selectively movable based on the width of the slot and whether the retaining pin is in the first position or the second position.

14. The knuckle joint assembly of claim 13, wherein the slot has a keyhole shape wherein a narrower portion of the keyhole corresponds to the narrower width of the slot and a round portion of the keyhole corresponds to the larger width of the slot.

15. The knuckle joint assembly of claim 13, wherein the retaining pin in the first position has a width that is less than the narrower width slot so that the retaining pin slides within the slot as the retaining clip is moved between the disengaged position and the engaged position.

16. The knuckle joint assembly of claim 13, wherein the retaining pin in the second position has a width that is greater than the narrower width slot so that the retaining pin is unable to slide from the larger width slot to the narrower width slot which blocks movement of the retaining clip from the engaged position.

17. The knuckle joint assembly of claim 13, further comprising a retaining clip guide configured to restrain the retaining clip in two axes of motion including vertical motion and side to side motion so that the retaining clip moves along the direction of the slot.

18. The knuckle joint assembly of claim 1, further comprising a knuckle joint housing cover connectable to the knuckle joint housing to cover the knuckle joint housing, wherein when the retaining clip is in a disengaged position the retaining clip blocks the cover from being connectable to the knuckle joint housing.

* * * * *